US007887485B2

(12) United States Patent
Karasawa

(10) Patent No.: US 7,887,485 B2
(45) Date of Patent: Feb. 15, 2011

(54) ULTRASONIC IMAGE BOUNDARY EXTRACTING METHOD, ULTRASONIC IMAGE BOUNDARY EXTRACTING APPARATUS, AND ULTRASONIC IMAGING APPARATUS

(75) Inventor: Hiroyuki Karasawa, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1511 days.

(21) Appl. No.: 11/235,412

(22) Filed: Sep. 27, 2005

(65) Prior Publication Data
US 2006/0079777 A1 Apr. 13, 2006

(30) Foreign Application Priority Data
Sep. 29, 2004 (JP) ............................. 2004-283335

(51) Int. Cl.
*A61B 8/00* (2006.01)
(52) U.S. Cl. ........................................ 600/443; 600/437
(58) Field of Classification Search ................. 600/443, 600/437–461
See application file for complete search history.

(56) References Cited

U.S. PATENT DOCUMENTS

| 6,839,456 B2 * | 1/2005 | Touzawa et al. ............ 382/128 |
| 2003/0092993 A1 * | 5/2003 | Grunwald .................... 600/462 |
| 2005/0075565 A1 * | 4/2005 | Satoh ......................... 600/437 |

FOREIGN PATENT DOCUMENTS

| JP | 07-008487 A | 1/1995 |
| JP | 08-117225 A | 5/1996 |
| JP | 08-206117 A | 8/1996 |
| JP | 10-258052 A | 9/1998 |
| JP | 2000-107183 A | 4/2000 |
| JP | 2000-126182 A | 5/2000 |
| JP | 2002-291750 A | 10/2002 |
| JP | 2003250804 A | 9/2003 |
| JP | 2004129773 A | 4/2004 |
| WO | WO 00/40997 A1 | 7/2000 |

OTHER PUBLICATIONS

Japanese Office Action corresponding to Japanese Patent Application No. 2004-283335, dated Mar. 16, 2010.

* cited by examiner

*Primary Examiner*—Brian Casler
*Assistant Examiner*—John F Ramirez
(74) *Attorney, Agent, or Firm*—Sughrue Mion, PLLC

(57) ABSTRACT

An ultrasonic image boundary extracting apparatus capable of accurately extracting outlines of tissues based on reception signals respectively output from ultrasonic transducers by receiving ultrasonic echoes. The ultrasonic image boundary extracting apparatus includes: an analysis unit for obtaining an interrelationship among plural reception signals with respect to a region within an object to be inspected from among reception signals obtained by transmitting ultrasonic waves toward the object from plural ultrasonic transducers and receiving ultrasonic waves reflected from the object; and a boundary detection unit for detecting a boundary between plural different tissues within the object based on the interrelationship to thereby generate information on a tissue boundary.

8 Claims, 23 Drawing Sheets

FIG.11

|  | $\beta < 1$ | $\beta = 1$ | $1 < \beta < 2$ | $\beta = 2$ | $\beta > 2$ |
|---|---|---|---|---|---|
| $\alpha < 1$ | U-SHAPED | J-SHAPED | J-SHAPED | J-SHAPED | J-SHAPED |
| $\alpha = 1$ | J-SHAPED | UNIFORM | J-SHAPED | J-SHAPED (STRAIGHT LINE) | J-SHAPED |
| $1 < \alpha < 2$ | J-SHAPED | J-SHAPED | SINGLE-PEAKED | SINGLE-PEAKED | SINGLE-PEAKED |
| $\alpha = 2$ | J-SHAPED | J-SHAPED (STRAIGHT LINE) | SINGLE-PEAKED | SINGLE-PEAKED | SINGLE-PEAKED |
| $\alpha > 2$ | J-SHAPED | J-SHAPED | SINGLE-PEAKED | SINGLE-PEAKED | SINGLE-PEAKED |

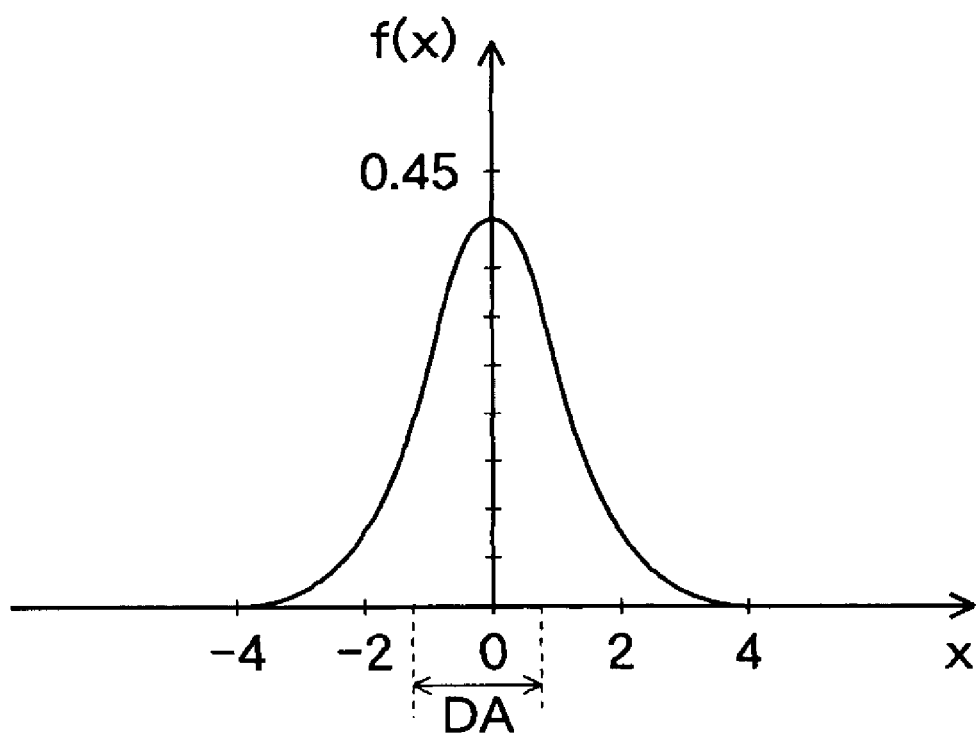

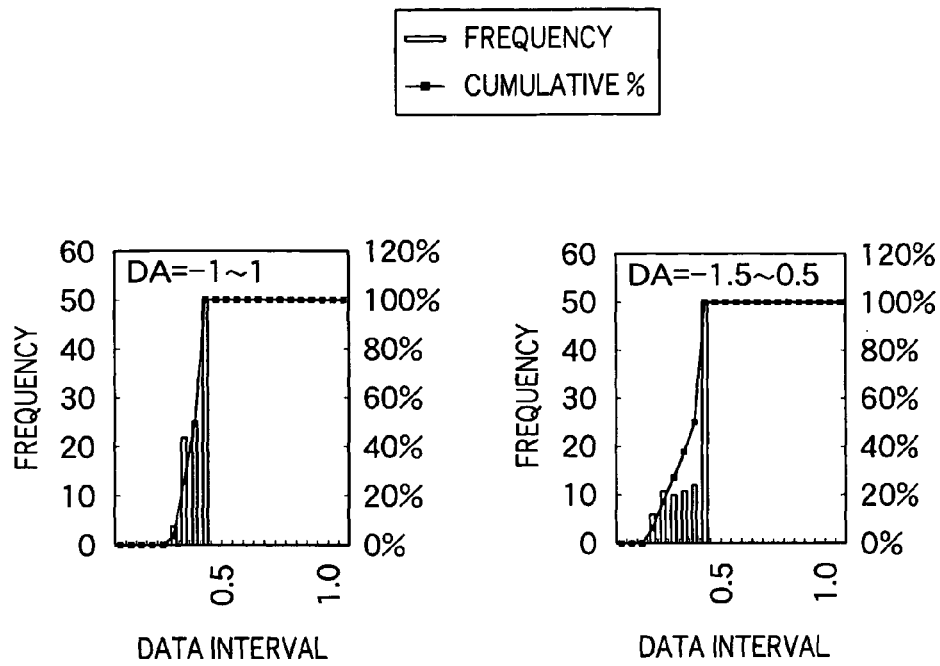
*FIG.15A*  *FIG.15B*
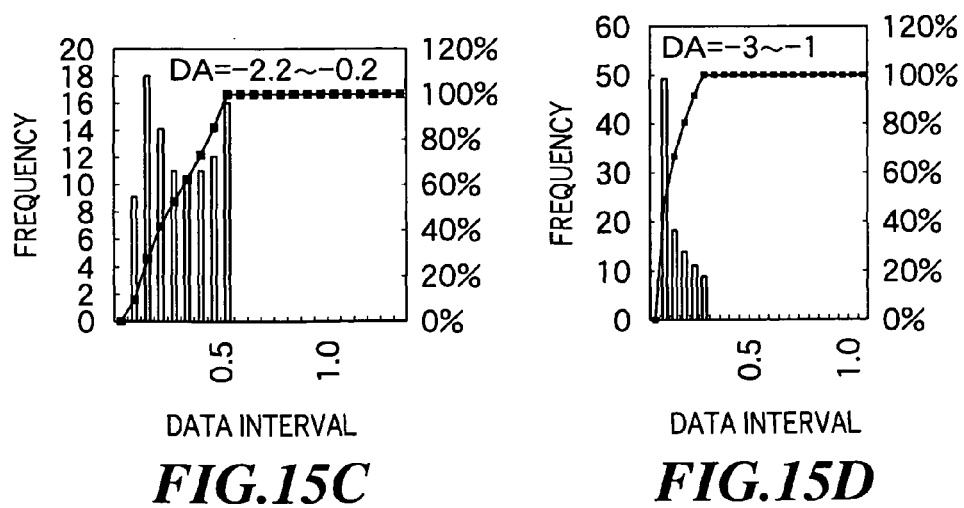
*FIG.15C*  *FIG.15D*

SOUND RAY DIRECTION

ULTRASONIC IMAGE BOUNDARY EXTRACTING METHOD, ULTRASONIC IMAGE BOUNDARY EXTRACTING APPARATUS, AND ULTRASONIC IMAGING APPARATUS

BACKGROUND OF THE INVENTION

1. Field of the Invention

The present invention relates to an ultrasonic imaging apparatus for transmitting and receiving ultrasonic waves to perform imaging of organs, bones, etc. within a living body thereby generating ultrasonic images to be used for diagnosis. Further, the present invention relates to an ultrasonic image boundary extracting method and an ultrasonic image boundary extracting apparatus to be used in the ultrasonic imaging apparatus.

2. Description of a Related Art

In an ultrasonic imaging apparatus to be used for medical diagnoses, an ultrasonic probe including plural ultrasonic transducers having transmitting and receiving functions of ultrasonic waves is used. When an ultrasonic beam formed by synthesizing plural ultrasonic waves is transmitted from such an ultrasonic probe to an object to be inspected, the ultrasonic beam is reflected at a boundary between regions having different acoustic impedances, i.e., between tissues within the object. Thus generated ultrasonic echoes are received and an image is constructed based on the intensity of the ultrasonic echoes, and thereby, the state within the object can be reproduced on a screen.

In such an ultrasonic image, conventionally, it has been attempted to easily and accurately extract outlines (boundaries) of tissues. This is because the extraction of outlines can be utilized for three-dimensional image processing, diagnoses of determination whether a tumor is benign or malignant, and so on.

As a related art, Japanese Patent Application Publication JP-A-8-206117 discloses an ultrasonic imaging apparatus for receiving ultrasonic waves reflected within the object to obtain image data corresponding to each point within a tomographic plane spreading within an object to be inspected in order to objectively extract outlines of tissues without manual operation by an operator or with simple manual operation. The ultrasonic imaging apparatus includes gradient computing means for obtaining gradients of the image data with respect to plural points within the tomographic plane, scalar quantity computing means for obtaining scalar quantities corresponding to the gradients with respect to plural points within the tomographic plane, local maximum point computing means for obtaining plural local maximum points within the tomographic plane where the scalar quantities are local maximums, and outline extracting means for obtaining an outline of a tissue within the object based on the plural local maximum points (page 1, FIG. 1).

JP-P2002-291750A discloses a tumor boundary display apparatus for an ultrasonic image for transmitting ultrasonic waves to the living body and receiving them, and displaying ultrasonic tomographic images within a living body in order to objectively determine a boundary matching vision by approximating a tumor boundary with a polygon and calculating brightness gradients in directions perpendicular to the respective sides. The tumor boundary display apparatus includes tumor boundary approximating means for approximating a visual tumor boundary on the ultrasonic tomographic image with a polygon, selecting means for selecting the respective points inside and outside of the polygon along perpendicular directions from the respective sides of the polygon obtained by the tumor boundary approximating means, brightness gradient extracting means for extracting brightness gradients of the respective points inside and outside of the polygon selected by the selecting means, brightness gradient comparing means for obtaining points indicating the maximum values of rates of change in brightness gradient extracted by the brightness gradient extracting means, and automatically tumor boundary correcting means for determining the points indicating the maximum values obtained by the brightness gradient comparing means as a tumor boundary (page 1, FIG. 3).

JP-P-2000-107183A discloses an organ boundary extracting apparatus including initial point designating means for receiving input of an initial point from an operator, search range setting means for setting a range where a new boundary point is searched for based on a known boundary point, search line setting means for setting a search line from the known boundary point, smoothing means for smoothing of pixel values surrounding the search line, gradient computing means for calculating a derivative value in a search line direction by calculating a gradient on the search line, boundary point determining means for determining a boundary point position based on the derivative value on the search line, and boundary forming means for forming a boundary line from a derived boundary point in order to reduce a possibility of outputting incorrect positions as a boundary from noise or a pixel value distribution similar to an organ boundary by setting a search range according to a shape of a boundary (page 2, FIG. 20).

JP-A-7-8487 discloses an ultrasonic image processing apparatus including a three dimensional data memory for storing echo data retrieved by transmitting and receiving ultrasonic waves in a three-dimensional region within a living body, boundary extracting means for extracting a tissue boundary based on the echo data, and image forming means for forming an ultrasonic image by utilizing the extracted boundary in order to correctly and rapidly perform surface extraction of a tissue for formation of an ultrasonic three-dimensional image (page 2). The boundary extracting means includes first variance value computing means for obtaining variance values by direction of the echo data with respect to each of plural reference directions intersecting at coordinates of interest and three-dimensionally spreading, second variance value computing means for obtaining a boundary value of a pixel of interest by further computing a variance value from the plural variance values by direction, and boundary determining means for determining whether the coordinates of interest is at a boundary point or not.

JP-P2000-126182A discloses a tumor diagnostic method of finding a tumor (especially, mammary tumor) region from a three dimensional image with high precision and automatically extracting determination of malignant tumor with high reproducibility (page 1). The tumor diagnostic method including the steps of quantifying concavo-convex irregularities of a tumor surface shape by defining a parameter S/V-ratio of a ratio of surface area S to volume V of a (benign or malignant) tumor extracted as a three-dimensional image by using a visualizing technology such as an ultrasonic diagnostic method and finding a cancer tissue from normal tissues by extracting boundaries between tissues represented by a three-dimensional image formed by an MRI image, ultrasonic image, or the like of a living body.

On the other hand, recent years, when an ultrasonic image is generated, the use of elements other than intensity of ultrasonic echoes has been studied. It is conceivable that statistical property (statistics values) that represents interrelationship among plural ultrasonic echo signals respectively received by plural ultrasonic transducers is utilized as the elements.

International Publication WO00/40997 discloses that, in order to properly suppress incoherent data in a coherent imaging system, the obtained echo signals are processed along both processing paths of a receive signal processing path using time delays set for traditional coherent receive beam forming and a receive signal processing path using time delays set to apply incoherent summing using time delays equal to zero, for example, and an ultrasonic image is generated based on thus obtained coherent summation signals and incoherent summation signals (page 1). Further, in WO00/40997, an image is generated based on a coherence factor, and displayed as a color map overlaid on a B-mode image. Here, the coherence factor refers to the degree of similarity of a signal that has been phase matched (coherent summed signal A) and a signal that has not been phase matched (incoherent summed signal B), and expressed by the difference between the signal A and signal B, the ratio of the signal A to the signal B, or the like. According to WO00/40997, it can be expected that the image quality of an ultrasonic image may be improved by making a choice among reception signals based on the coherence factor. However, tissue boundaries or angles of reflection surfaces to ultrasonic beams are not obtained.

JP-A-8-117225 discloses a living tissue evaluation apparatus including transmitting means for transmitting ultrasonic waves to a living tissue, intensity distribution obtaining means for obtaining an intensity distribution of ultrasonic waves by receiving ultrasonic waves transmitted through the living tissue and spread, and evaluation value computing means for calculating an evaluation value of the living tissue based on the obtained intensity distribution for analyzing a microscopic structure of the living body by utilizing the intensity distribution of ultrasonic waves transmitted through the living tissue (page 1).

However, in JP-A-8-117225, since an interference phenomenon in transmission is used, information on the depth direction of the ultrasonic beam can not be obtained. Further, any information can not be obtained within objects except for an object within which ultrasonic interference occurs. Furthermore, in JP-A-8-117225, although an intensity distribution among plural reception signals obtained by plural ultrasonic vibrators is obtained and the living tissue is evaluated based on the intensity distribution, boundaries between different tissues are not detected.

JP-A-10-258052 discloses a wave receiving apparatus including a receiver for receiving wave that has reached within an aperture with information on a position within the aperture, a weighting processing unit for performing weighting processing with respective plural kinds of weighting functions using the position within the aperture as a variable, and a computing unit for performing a computation including a computation for obtaining a propagation direction of the wave that has reached within the aperture or a position of a wave source that has generated the wave based on plural weighted reception signals obtained by the weighting processing in the weighting processing unit in order to detect orientation or displacement of a target of detection by one reception with a aperture in an arbitrary position and obtain high resolving power and obtain signals equivalent of reception signals corresponding to an aperture that has not actually received (page 1).

In JP-A-10-258052, although the orientation and position of the target of detection are detected by weighting the reception signals according to the position within the aperture, mutual property and statistics values of reception signals obtained from plural ultrasonic transducers are not utilized.

In all of the above-mentioned JP-A-8-206117, JP-P-2002-291750A, JP-P2000-107183A, JP-A-7-8487 and JP-P2000-126182A, property of image signals such as intensity of image signals (i.e., brightness), derivative values thereof, variances, and statistics values are used as data for extracting boundaries. Since the image signals are generated based on the intensity of ultrasonic echoes obtained by reflection of ultrasonic waves at boundaries of tissues, they are susceptible to various factors such as surface property of tissues (irregularities and hardness/softness). Accordingly, even when boundaries are detected by utilizing such image signals, sometimes precision is low and tissues other than boundaries are incorrectly detected. Further, the detection precision often becomes unstable due to gradation of brightness or the like.

Further, purposes of the above-mentioned WO00/40997, JP-8-117225 and JP-A-10-258052 are to exclusively improve image quality of ultrasonic images, and extraction of tissue boundaries is not performed.

SUMMARY OF THE INVENTION

The present invention has been achieved in view of the above-mentioned problems. A first object of the present invention is to accurately extract boundaries between plural different tissues (outlines of tissues) based on reception signals (ultrasonic echo signals) respectively output from ultrasonic transducers. Further, a second object of the present invention is to generate ultrasonic images with higher accuracy and resolving power by detecting angles of extracted boundaries relative to an ultrasonic transmission direction.

In order to solve the above-described problems, an ultrasonic image boundary extracting method according to one aspect of the present invention includes the steps of: (a) obtaining an interrelationship among plural reception signals with respect to a region within an object to be inspected from among reception signals obtained by transmitting ultrasonic waves toward the object from plural ultrasonic transducers and receiving ultrasonic waves reflected from the object; and (b) detecting a boundary between plural different tissues within the object based on the interrelationship to thereby generate information on a tissue boundary.

Further, an ultrasonic image boundary extracting apparatus according to one aspect of the present invention includes: analysis means for obtaining an interrelationship among plural reception signals with respect to a region within an object to be inspected from among reception signals obtained by transmitting ultrasonic waves toward the object from plural ultrasonic transducers and receiving ultrasonic waves reflected from the object; and boundary detecting means for detecting a boundary between plural different tissues within the object based on the interrelationship to thereby generate information on a tissue boundary.

Furthermore, an ultrasonic imaging apparatus according to one aspect of the present invention includes: an ultrasonic probe including plural ultrasonic transducers for transmitting ultrasonic waves toward an object to be inspected and receiving ultrasonic waves reflected from the object to output reception signals; analysis means for obtaining an interrelationship among plural reception signals with respect to a region within the object from among the reception signals respectively output from the plural ultrasonic transducers; boundary detecting means for detecting a boundary between plural different tissues within the object based on the interrelationship to thereby generate information on a tissue boundary; boundary image data generating means for generating image data representing the detected boundary based on the information on the tissue boundary; and B-mode image data generating means for performing phase matching on the reception signals respectively output from the plural ultrasonic transducers to generate B-mode image data.

According to the present invention, since whether or not a region as a target of analysis is a tissue boundary is determined based on the interrelationship among plural reception signals, boundaries between plural different tissues can be easily and accurately extracted. Accordingly, by using thus extracted boundaries, an ultrasonic image with high image quality can be generated, in which the state within the object is accurately represented. Further, various measurement quantities usable in diagnoses of disease tissues can be accurately calculated based on the extracted boundaries. As a result, the quality and efficiency of medical diagnoses can be improved.

BRIEF DESCRIPTION OF THE DRAWINGS

FIG. 11 is a chart showing classified parameters of a beta distribution;

FIG. 14 shows a spatial intensity distribution in the case where a beta distribution becomes J-shaped;

FIGS. 15A to 15D are histograms corresponding to the spatial intensity distribution shown in FIG. 14;

DESCRIPTION OF THE PREFERRED EMBODIMENTS

Figure 1:
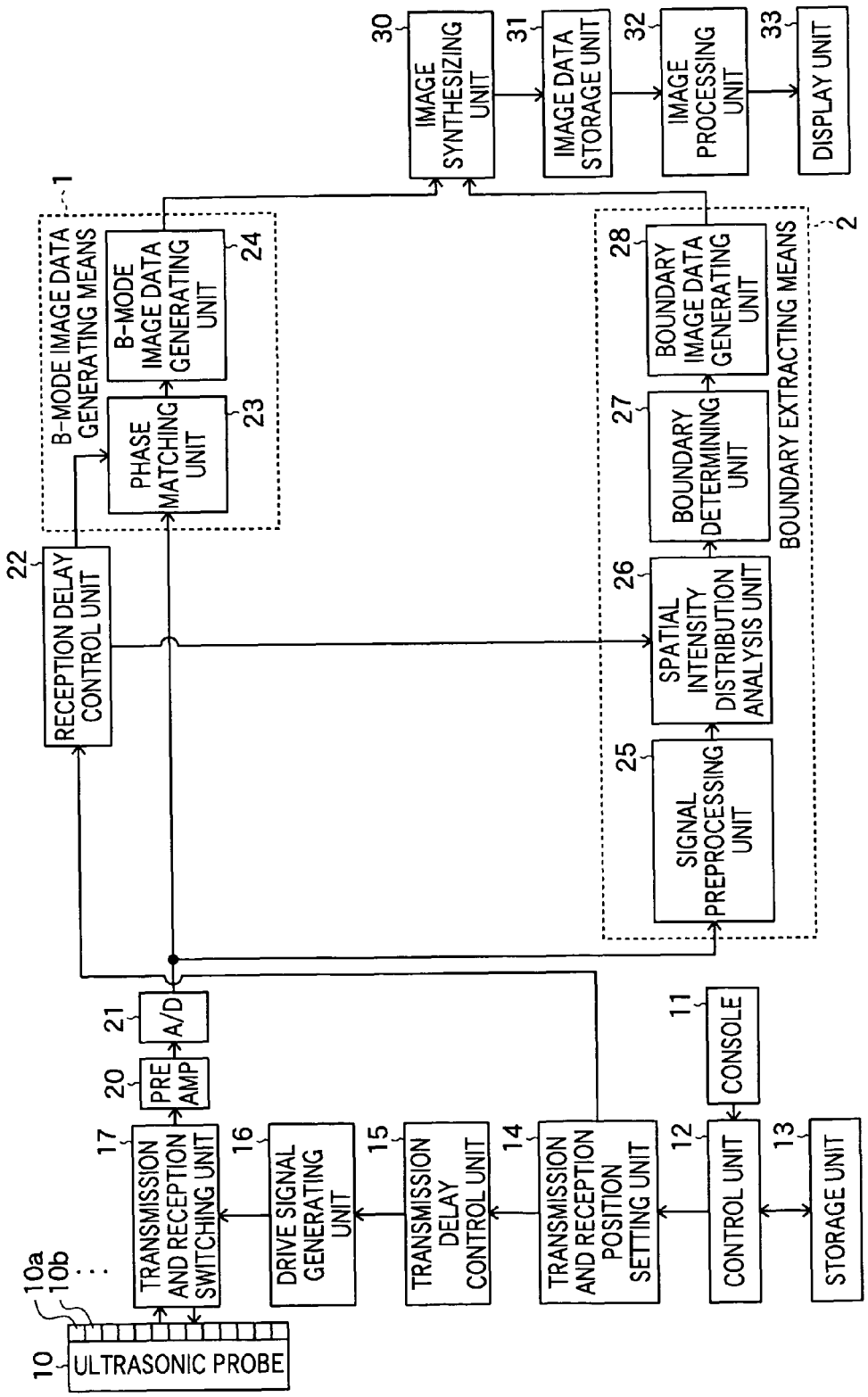
FIG. 1 is a block diagram showing a constitution of an ultrasonic imaging apparatus according to the first embodiment of the present invention.

Hereinafter, preferred embodiments of the present invention will be described in detail by referring to the drawings. The same reference numbers are assigned to the same component elements and the description thereof will be omitted.

FIG. 1 is a block diagram showing a constitution of an ultrasonic imaging apparatus according to the first embodiment of the present invention. The ultrasonic imaging apparatus according to the embodiment has not only a function of generating B-mode image (B-mode image generating means 1 in FIG. 1) which is owned by a general ultrasonic imaging apparatus, but also a function of extracting boundaries between plural different tissues (boundary extracting means 2 in FIG. 1).

As shown in FIG. 1, the ultrasonic imaging apparatus according to the present invention includes an ultrasonic probe 10, a console 11, a control unit 12, a storage unit 13, a transmission and reception position setting unit 14, a transmission delay control unit 15, a drive signal generating unit 16, and a transmission and reception switching unit 17.

The ultrasonic probe 10 is used by being abutted on the object to transmit ultrasonic waves to an object to be inspected and receive ultrasonic waves reflected from the object. The ultrasonic probe 10 includes plural ultrasonic transducers 10a, 10b, . . . for transmitting ultrasonic beams based on applied drive signals, receiving propagating ultrasonic echoes to output reception signals. These ultrasonic transducers 10a, 10b, . . . are arranged in a one-dimensional or two-dimensional manner to form a transducer array.

Each ultrasonic transducer is constituted by a vibrator in which electrodes are formed on both ends of a material having a piezoelectric property (piezoelectric material) such as a piezoelectric ceramic represented by PZT (Pb (lead) zirconate titanate), a polymeric piezoelectric material represented by PVDF (polyvinylidene difluoride), or the like. When a voltage is applied to the electrodes of the vibrator by transmitting pulse electric signals or continuous wave electric signals, the piezoelectric material expands and contracts. By the expansion and contraction, pulse ultrasonic waves or continuous wave ultrasonic waves are generated from the respective vibrators, and an ultrasonic beam is formed by synthesizing these ultrasonic waves. Further, the respective vibrators expand and contract by receiving propagating ultrasonic waves and generate electric signals. These electric signals are output as reception signals of ultrasonic waves.

Alternatively, as the ultrasonic transducers, plural kinds of elements of different conversion types may be used. For example, the above-mentioned vibrators are used as elements for transmitting ultrasonic waves and photo-detection type ultrasonic transducers are used as elements for receiving ultrasonic waves. The photo-detection type ultrasonic transducer is for detecting ultrasonic waves by converting ultrasonic signals into optical signals, and constituted by a Fabry-Perot resonator or fiber Bragg grating, for example.

The console 11 is used when an operator inputs commands and information to the ultrasonic imaging apparatus. The console 11 includes a keyboard, adjustment knob, and a pointing device including mouse, or the like.

The control unit 12 is formed by a CPU and software, for example, and controls the respective units of the ultrasonic imaging apparatus based on the commands and information input from the console 11. In the storage unit 13, programs for allowing the CPU that forms the control unit 12 to execute operation or the like are stored.

The transmission and reception position setting unit 14 sets the transmission direction, reception direction, and depth of focus of the ultrasonic beam transmitted from the ultrasonic probe 10 and the aperture diameter of the ultrasonic transducer array (i.e., plural ultrasonic transducers to be used) in order to scan a region within the object by the ultrasonic beam. Further, the transmission delay control unit 15 sets delay times to be provided to the plural ultrasonic transducers for transmitting the ultrasonic beam that has been set by the transmission and reception position setting unit 14.

The drive signal generating unit 16 includes plural drive circuits for generating plural drive signals to be supplied to the plural ultrasonic transducers, respectively. These drive circuits generates drive signals based on the delay times that have been set in the transmission delay control unit 15.

The transmission and reception switching unit 17 switches between a transmission mode in which drive signals are supplied to the ultrasonic probe 10 and a reception mode in which reception signals are output from the ultrasonic probe 10 under the control of the control unit 11.

Further, the ultrasonic imaging apparatus according to the embodiment includes a preamplifier (PREAMP) 20, an A/D converter 21, a reception delay control unit 22, the B-mode image data generating means 1, the boundary extracting means 2, an image synthesizing unit 30, an image data storage unit 31, an image processing unit 32, and a display unit 33.

The preamplifier 20 and the A/D converter 21 have plural channels corresponding to the plural ultrasonic transducers 10a, 10b, . . . , input reception signals output from the plural ultrasonic transducers and perform preamplification and analog/digital conversion on the respective reception signals.

The reception delay control unit 22 has plural delay patterns (phase matching patterns) corresponding to the reception direction and focal depth of the ultrasonic echoes, and selects delay patterns to be provided to the plural reception signals according to the reception direction and focal depth that have been set by the transmission and reception position setting unit 14 and supplies them to a phase matching unit 23 and a spatial intensity distribution analysis unit 26.

The B-mode image data generating means 1 includes a phase matching unit 23 and a B-mode image generating unit 24.

The phase matching unit 23 performs reception focus processing by providing delays to the plural reception signals (reception data) that have been A/D converted, respectively, based on the delay pattern that has been supplied from the reception delay control unit 22, and adding the signals. By the reception focus processing, sound ray signals (sound ray data) in which focal points of ultrasonic echoes are narrowed are formed.

The B-mode image data generating unit 24 generates B-mode image data by performing envelope detection processing and STC (sensitivity time gain control) on the sound ray data that has been formed in the phase matching unit 23.

On the other hand, the boundary extracting means 2 includes a signal preprocessing unit 25, a spatial intensity distribution analysis unit 26, a boundary detection unit 27, and a boundary image data generating unit 28.

The signal preprocessing unit 25 performs the following intensity corrections (i) to (iii) according to need on the plural reception signals that have been A/D converted.

(i) Element Sensitivity Correction

Variations in performance of ultrasonic transducers generated when an ultrasonic transducer array is manufactured are corrected. The correction can be performed in the manner in which a correction table is created in advance by transmitting and receiving ultrasonic beams from the ultrasonic probe 10 using a standard reflection source and measuring the characteristics of the respective ultrasonic transducers, and the correction table is used at the time of processing of reception signals.

(ii) Solid Angle Intensity Correction

In an ultrasonic transducer array, since the solid angle relative to the reflection position of the ultrasonic echo becomes smaller, as an ultrasonic transducer is located closer to the end of the aperture, apparent reception intensity becomes smaller. Accordingly, intensity correction is performed on the reception signals according to the reception depth (the depth of the reflection position of the ultrasonic echoes), positional relationship with the respective ultrasonic transducers, and differences in reception solid angle between ultrasonic transducers determined by the aperture.

(iii) Distance Correction

The distance attenuation of the ultrasonic echoes that varies depending on the reception depth and positional relationship with the respective ultrasonic transducers are corrected. Since the amount of correction differs depending on the part to be observed, standard values according to parts to be observed may be set as default values in advance, and the operator may change the setting value while watching the displayed image.

Further, the signal preprocessing unit 25 performs processing such as smoothing and envelope detection on the corrected reception signals and converts those reception signals into digital signals. Thus, the envelope detection processing before data analysis for tissue property image generation can suppress the influence by the noise and reduce the calculation amount in the subsequent processing. Furthermore, as described below, the boundary image data generated by the boundary image data generating unit 28 can be superimposed on the B-mode image data without change.

The spatial intensity distribution analysis unit 26 generates information representing tissue property of reflectors within the object by obtaining a spatial intensity distribution (hereinafter, simply referred to as "intensity distribution") of the plural reception signals on the same phase matching line among the plural reception signals processed by the signal preprocessing unit 25 and analyzing them. These plural reception signals on the same phase matching line are determined based on the delay pattern supplied from the reception delay control unit 22. Here, the tissue property of reflectors includes not only the surface conditions (surface property) such that the reflector surface is hard (e.g., bone part, tendon, and ligament) or soft (e.g., skin and muscle), but also that the tissue is a uniform internal tissue, speckle component, or the like. Further, the information representing tissue property of reflectors includes statistics values representing the characteristics of such tissue property of reflectors.

The boundary detection unit 27 detects a boundary (outline) of the reflector based on the information representing tissue property of the reflector generated by the spatial intensity distribution analysis unit 26, using the information as parameters.

The boundary image data generating unit 28 generates boundary image data by assigning predetermined colors to regions (display regions) on a display screen corresponding to boundaries that have been detected by the boundary detection unit 27.

The principle of boundary extraction performed in the boundary extracting means 2 and an operation of the boundary extracting means 2 will be described later in detail.

The image synthesizing unit 30 generates synthesized image data in which a boundary image is superimposed upon corresponding regions of the B-mode image based on the B-mode image data generated by the B-mode image generating unit 24 and the boundary image data generated by the boundary image data generating unit 28. The regions on the B-mode image on which the tissue property image is to be superimposed may be automatically determined by the image synthesizing unit 30, or may be manually designated by the operator using the console 11.

The image data storage unit 31 stores generated synthesized image data. Further, the image processing unit 32 generates image data for screen display by performing predetermined image processing including scan conversion, gradation processing, and the like on the synthesized image data. The display unit 33 includes a display device such as a CRT or LCD, and displays an ultrasonic image based on the image data that has been image processed in the image processing unit 32.

Next, the principle of boundary extraction will be described.

Figure 2A:
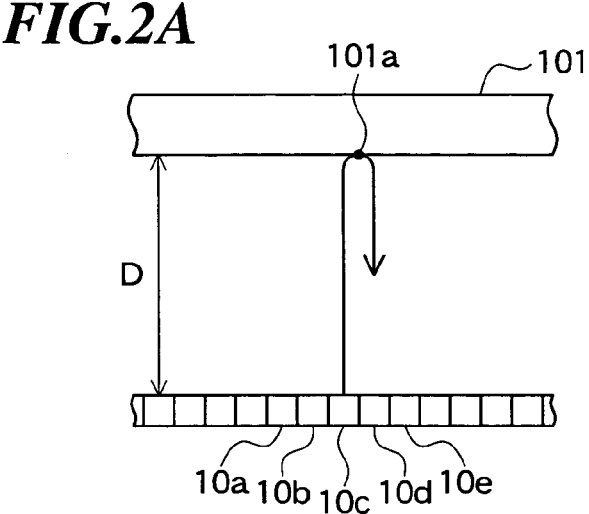
FIGS. 2A to 2C show an intensity distribution of reception signals when ultrasonic waves are transmitted toward a specular reflector and received.
Figure 2B:
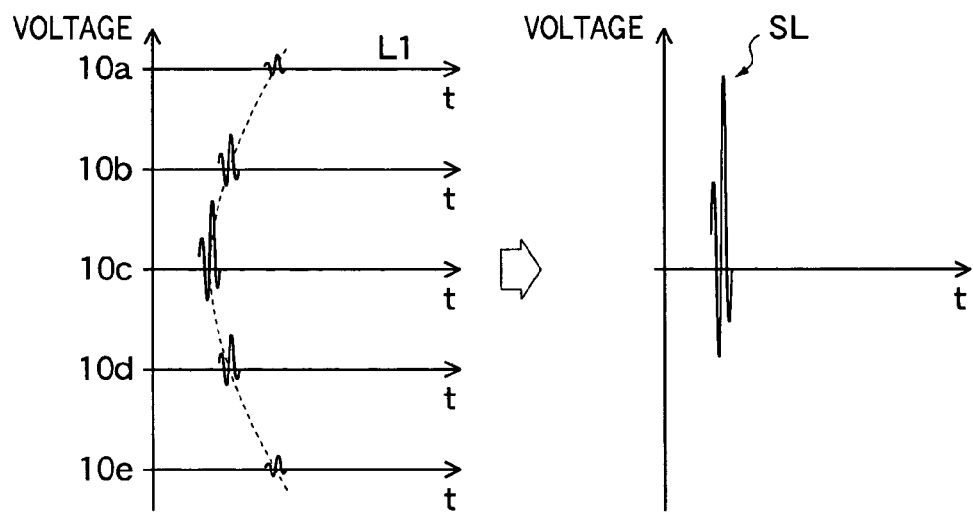
Figure 2C:
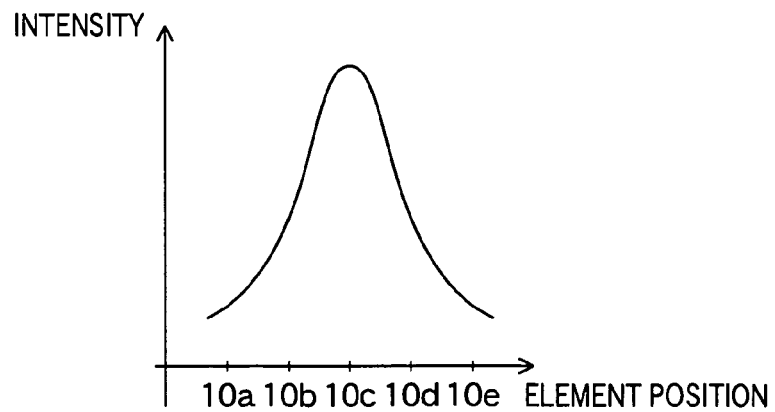

First, as shown in FIG. 2A, a case will be considered where an ultrasonic beam is transmitted toward a reflector 101 and an ultrasonic echo reflected on the surface of the reflector 101 located at depth "D" is received by using an ultrasonic transducer array including ultrasonic transducers 10a to 10e. FIG. 2B shows reception waveforms of ultrasonic echoes at the ultrasonic transducers 10a to 10e. In FIG. 2B, the horizontal axis indicates time (t) and the vertical axis indicates voltage of reception signal. Further, FIG. 2C shows an intensity distribution of the reception signals output from the ultrasonic transducers 10a to 10e. In FIG. 2C, the horizontal axis indicates position of ultrasonic transducer (element) and the vertical axis indicates intensity of reception signal.

The ultrasonic echoes reflected at reflection point 101a are first received by the ultrasonic transducer 10c right opposite to the reflection point 101a, and then, sequentially received by the ultrasonic transducers 10b and 10d and the ultrasonic transducers 10a and 10e as shown in FIG. 2B. In the case where the reflector 101 is an object that reflects the ultrasonic echoes with little scattering like a bone part, the ultrasonic echoes are received by the ultrasonic transducers 10a to 10e in an intensity distribution with the position of the ultrasonic transducer 10c as a peak thereof. As below, such a reflector (reflection surface) is called "specular reflector (specular reflection surface)", and the ease of specular reflection (i.e., difficulty of scattering) is called "specular reflectance".

In the case where the B-mode image is generated, a predetermined delay times are provided to the reception signals on the same phase matching line L1 and added them. Thereby, a sound ray signal SL representing ultrasonic information on a region including the reflection point 101a is formed.

Figure 3A:
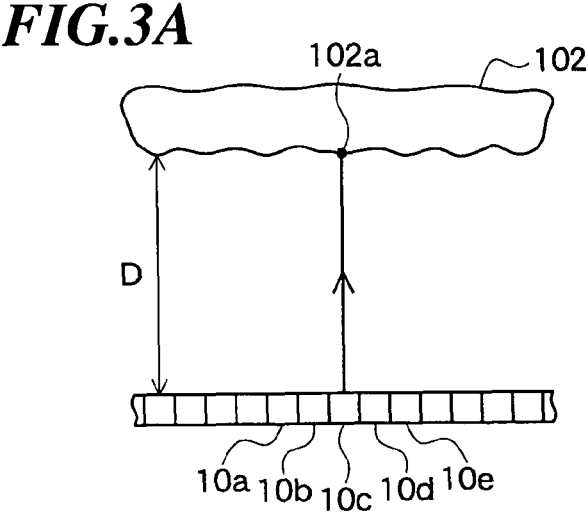
FIGS. 3A to 3C show an intensity distribution of reception signals when ultrasonic waves are transmitted toward a scattering reflector and received.
Figure 3B:
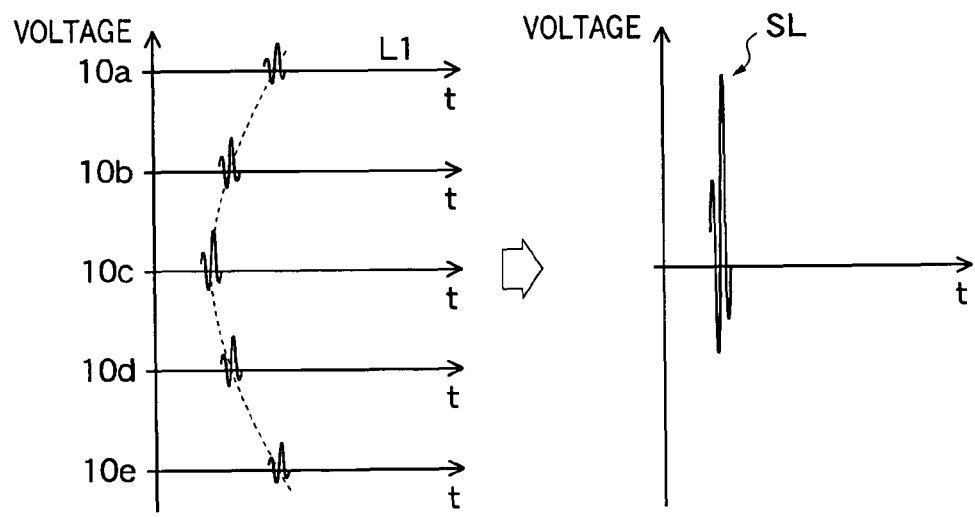

Next, the case where an ultrasonic beam is transmitted toward a reflector like a soft tissue that readily scatters ultrasonic waves will be considered. As below, such a reflector (reflection surface) is called "scattering reflector (scattering reflection surface)". As shown in FIG. 3A, when an ultrasonic beam is transmitted toward a scattering reflector 102 located at depth "D", the ultrasonic beam is scattered in various directions at reflection point 102a. Thus generated ultrasonic echoes are received by the ultrasonic transducers 10a to 10e with timing depending on the depth "D" and the position of the reflection point 102a as shown in FIG. 3B. Since the timing is on the phase matching line L1 like the case of the reception waveform of the ultrasonic echoes shown in FIG. 2B, when phase matching is performed for generating a B-mode image, the same sound ray signal SL as shown in FIG. 2B is formed.

Figure 3C:
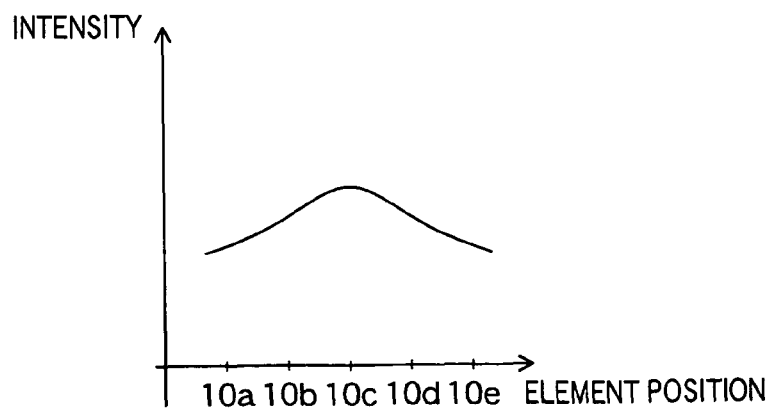

However, in the case where an ultrasonic beam is reflected by the scattering reflector, because the intensity of ultrasonic echoes is dispersed in various directions, the intensity distribution of the reception signals output from the ultrasonic transducers 10a to 10e becomes relatively flat as shown in FIG. 3C.

Figure 4A:
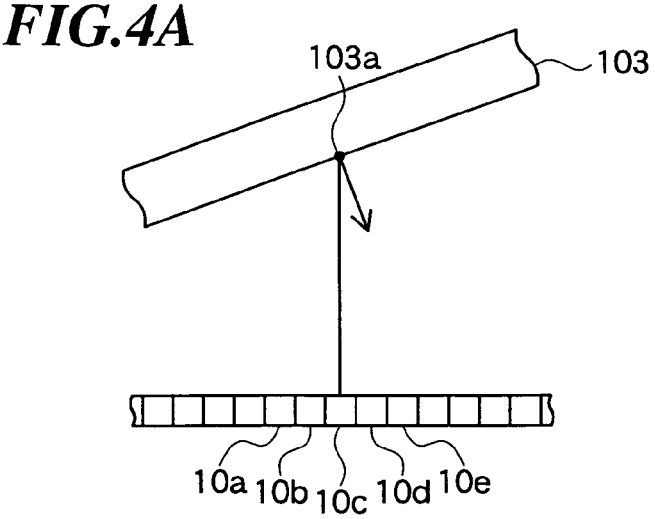
FIGS. 4A to 4C show an intensity distribution of reception signals when an ultrasonic beam is transmitted toward a inclined specular reflector and received.
Figure 4B:
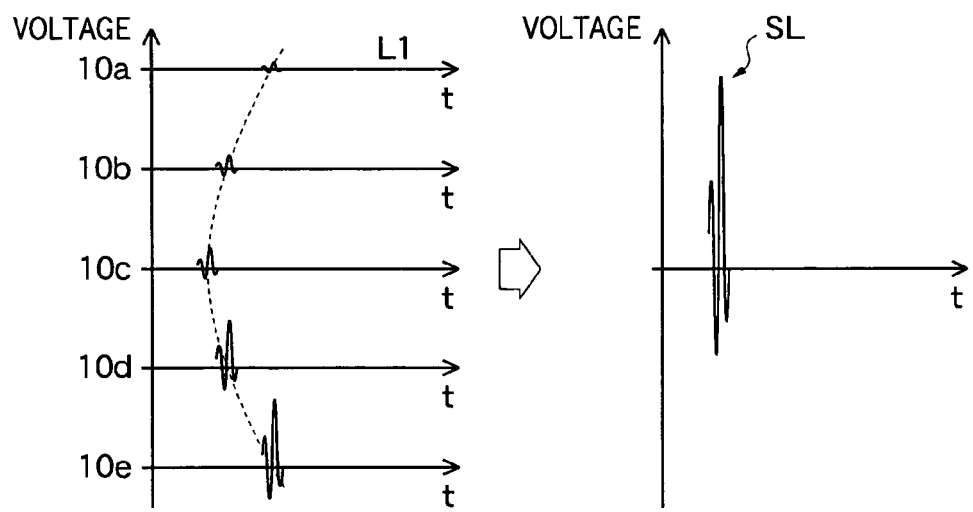

Next, the case where a specular reflector is inclined relative to the ultrasonic transducer array will be considered. As shown in FIG. 4A, when an ultrasonic beam is transmitted toward a specular reflector 103 located at depth "D", the ultrasonic beam is reflected in a direction different from the direction in which the ultrasonic beam has been transmitted according to the inclination of the specular reflector 103. Thus generated ultrasonic echoes are received by the ultrasonic transducers 10a to 10e with timing depending on the depth "D" and the position of the reflection point 103a. As shown in FIG. 4B, since the timing is on the phase matching line L1 like the case of the reception waveform of ultrasonic echoes shown in FIG. 2B, when phase matching is performed for generating a B-mode image, also the same sound ray signal SL as shown in FIG. 2B is formed.

Figure 4C:
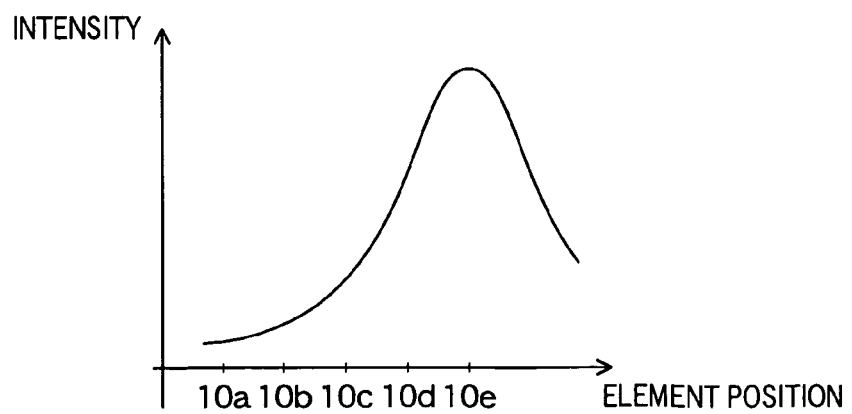

However, in the case where the ultrasonic beam is reflected by the reflector inclined relative to the ultrasonic transducer array, since the propagation direction of ultrasonic echoes is changed, the peak position is shifted in the intensity distribution of the reception signals output from the ultrasonic transducers 10a to 10e as shown in FIG. 4C.

Thus, when phase matching is performed on the reception signals, the sound ray signals representing the reflection position of the ultrasonic echoes (the boundary between tissues) are uniformly determined, and the tissue property and inclination of the reflector can be obtained by focusing attention on the interrelationship among plural reception signals (e.g., intensity distribution). Especially, the reflectance of a bone part becomes about hundred times the reflectance of a soft tissue, and therefore, it can be analyzed at the respective reception signal levels and the hard tissue and soft tissue can be sufficiently discriminated.

Next, an operation of the spatial intensity distribution analysis unit 26 through boundary image data generating unit 28 included in the boundary extracting means 2 will be described by referring to FIG. 5.

First, the spatial intensity distribution analysis unit 26 shown in FIG. 1 obtains an intensity distribution of plural reception signals with respect to a region as a target of analysis (analysis region). That is, in a graph having the horizontal axis as position coordinate of transducer and the vertical axis as intensity of reception signal, intensity of the reception signals on the same phase matching line output from the plural ultrasonic transducers within aperture diameter DA of the ultrasonic transducers is plotted. Then, in the intensity distribution chart, the horizontal axis is read as data value and the vertical axis is read as frequency from a different perspective. As shown in FIG. 5, thus obtained relationship diagram is handled as a frequency distribution chart representing the relationship between random probability "x" and probability density function f(x) as below.

Figure 5:
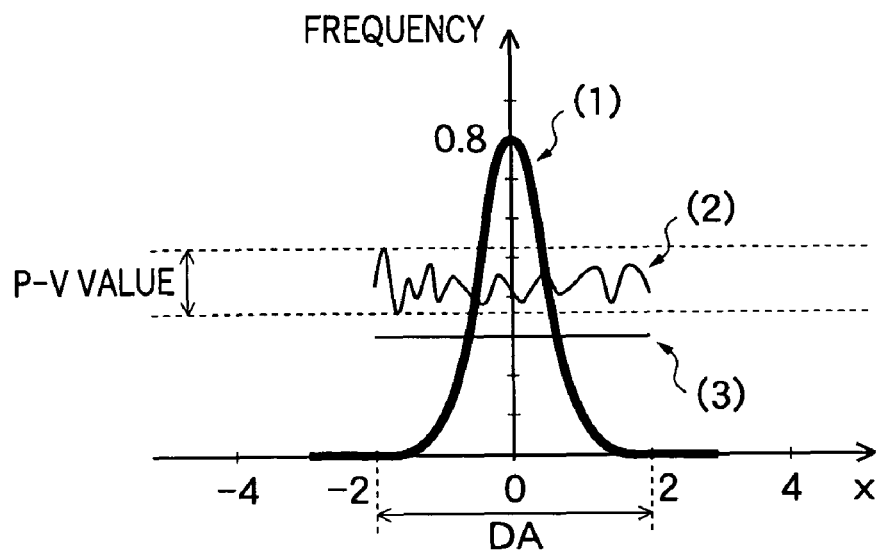
FIG. 5 shows a spatial intensity distribution of reception signals.

In FIG. 5, curve (1) represents a frequency distribution in the case where the frequency distribution is concentrated on a certain value, that is, an ultrasonic beam is reflected by a specular reflector. Further, curve (2) represents a frequency distribution in the case where the frequency is randomly distributed, that is, an ultrasonic beam is reflected by a scattering reflector. Furthermore, curve (3) shown for comparison represents a frequency distribution in the virtual case where an ultrasonic beam is reflected in plural directions with equal intensity.

The spatial intensity distribution analysis unit 26 calculates necessary statistics values of the following statistics values (1) to (5) based on the frequency distributions.

(1) Mean

A mean is used as a value representing quantitative characteristics of frequency. When an ultrasonic echo propagating from the front direction of the ultrasonic transducer array is received, the mean typically becomes zero (center), while, when a reflector is inclined relative to the ultrasonic transducer array, the mean is shifted from the center toward an end. Not only the typical arithmetic mean but also median or mode is used. Since the magnitude relationship between these arithmetic means, medians, or modes changes according to the distribution conditions of frequency, they can be used when variations in frequency are estimated.

(1-1) Median

A median refers to a value located at the center of the number of data in the case where the frequencies are arranged in order from the minimum value. When the number of data is even, the arithmetic mean of the center two values is used.

(1-2) Mode

A mode refers to a value with the highest frequency among frequencies.

(2) Variance

A variance is one of scales that indicate variations in frequency, and obtained by dividing sum of squares of deviation as differences between the respective detection data and arithmetic mean by the number of data (or the number of data-1). When the frequency distribution is close to the normal distribution and the peak rises as the curve (1), a variance value becomes smaller. Contrary, when the frequency distribution is random as the curve (2) or when the frequency distribution is uniform as the curve (3), a variance value becomes larger.

(3) Skewness

A skewness refers to a scale that indicates the degree of asymmetry around the mean of frequency, and is obtained by the following expression.

Skewness=(sum of cube of deviation)/(number of data)/(cube of standard deviation)

Zero of skewness represents that the frequency distribution is not deviated, and, in this case, the arithmetic mean, the median, and the mode become equal. Further, positive skewness represents that the frequency distribution is negatively deviated, and, in this case, the relationship arithmetic mean>median>mode holds. Furthermore, negative skewness represents that the frequency distribution is positively deviated, and, in this case, the relationship arithmetic mean<median<mode holds.

(4) Kurtosis

A kurtosis refers to a scale that indicates degree of concentration around the mean of frequency (sharpness), and is obtained by the following expression.

Kurtosis=(sum of biquadrate of deviation)/(number of data)/(cube of standard deviation)

Here, in a standard normal distribution having a mean of "0" and variance of "1", the kurtosis becomes "3". Accordingly, the kurtosis is evaluated with numeric value "3" as reference. That is, when the kurtosis is "3", the frequency distribution is close to the normal distribution. Further, the smaller than "3" the kurtosis becomes, flatter the frequency distribution becomes. Furthermore, the larger than "3" the kurtosis becomes, sharper the frequency distribution around the mean becomes.

(5) P-v Value, Square Mean Between Adjacent Elements, etc.

When the frequency is randomly distributed as the curve (2), a scale indicating the degree of random is also calculated. As such a scale, for example, as shown in FIG. 5, the distance between a peak and a valley (p-v value) in the curve (2), difference square mean between adjacent ultrasonic transducers, or the like is used. These scales show that, the larger the value, the more indefinite the ultrasonic echo is and larger the speckle component is.

Figure 6:
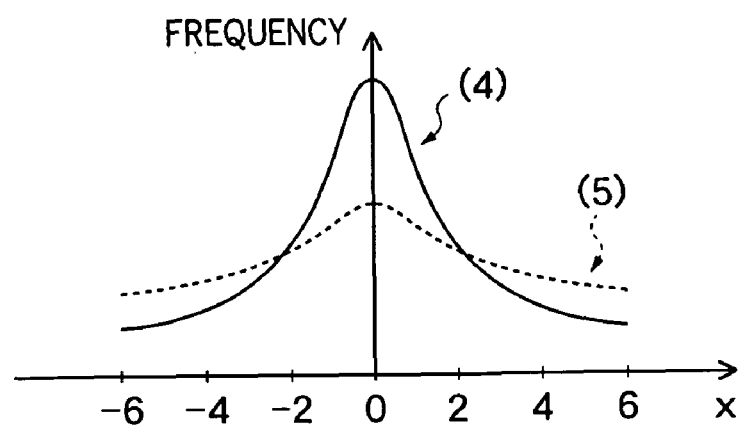
FIG. 6 is a diagram for explanation of a relationship between a spatial intensity distribution of reception signals and colors assigned to boundary image data.

The boundary detection unit 27 shown in FIG. 1 detects boundaries between tissues in an ultrasonic image by using statistics values calculated by the spatial intensity distribution analysis unit 26 as parameters so as to generate boundary information containing position information of boundaries. In this regard, for example, as shown by curve (4) in FIG. 6, the boundary detection unit 27 may detect a region where the variance is smaller than a predetermined threshold value as a boundary, or a region where the kurtosis is larger than a predetermined threshold value as a boundary. As a threshold value, for example, an average value of those statistics values within a certain region may be selected. Alternatively, the boundary detection unit 27 may determine a boundary based on the rate of change of those statistics values, i.e., a derivative value of the statistics values. In this case, since the boundary is emphasized, the boundary determination performance of the boundary detection unit 27 can be improved. Further, the boundary detection unit 27 may add the detected boundary property to boundary information. For example, a region may be determined to be a boundary with stronger specular reflectance (that is, a harder boundary) as the kurtosis is larger, and a boundary with weaker specular reflectance (that is, a softer boundary) as the kurtosis is smaller. Alternatively, for example, a region with a larger p-v value may be determined to be a boundary with greater scattering components.

The boundary image data generating unit 28 generates boundary image data representing boundary images by assigning predetermined colors to display regions corresponding to detected boundaries based on the boundary information generated by the boundary detection unit 27. In this regard, different colors in density may be assigned according to the strength of specular reflectance. For example, deep blue is assigned to a boundary with high specular reflectance, and pale blue is assigned to a boundary with low specular reflectance.

Figure 7:
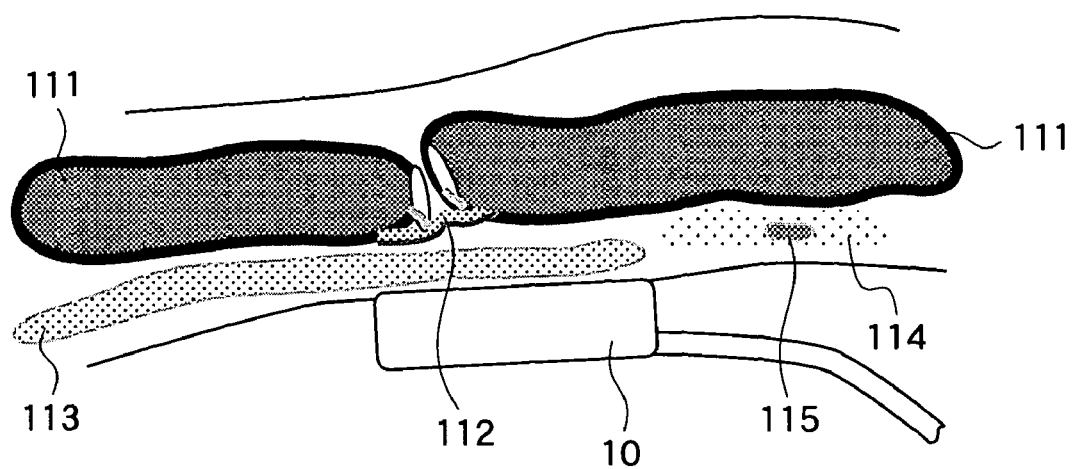
FIG. 7 is a schematic diagram showing a synthesized image of a B-mode image and a boundary image.

FIG. 7 schematically shows a synthesized image of a B-mode image and a boundary image. In an ultrasonic image shown in FIG. 7, surfaces (boundaries) of a bone part 111, tendon, a ligament 112, and a muscle tissue 113 are displayed in different colors according to tissue property (e.g., hardness). Further, a boundary of an abnormal tissue 115 is displayed inside of a speckle region 114. Thus, the ultrasonic image becomes easily viewable by extracting tissue boundaries and displaying them in different colors, and thereby, quality and efficiency of medical diagnoses can be improved. Especially, around a bone part or the like, tissue boundaries are distinctively imaged even when multiple reflection of ultrasonic waves occurs because of the bone, and thereby, tendons and muscles can be easily discriminated.

In the above-mentioned first embodiment of the present invention, different signal preprocessings have been performed in the B-mode image data generating means 1 and the boundary extracting means 2, however, a common preprocessing may be performed. For example, the signal preprocessing unit 25 shown in FIG. 1 may be located before the branch to the B-mode image data generating means 1 and the boundary extracting means 2. In this case, such signal preprocessing may be performed before A/D conversion of reception signals or after the A/D conversion.

Next, a modified example of the ultrasonic imaging apparatus according to the embodiment will be described.

In the boundary extracting means 2 shown in FIG. 1, the boundary detection unit 27 may generate boundary information based on the sound ray data generated in the phase matching unit 23 and the information representing surface property of the reflector generated in the spatial intensity distribution analysis unit 26. For example, the specular reflectance is determined with respect to a position where a peak of waveform appears in the sound ray data based on the statistics values such as variance and kurtosis, and thereby, boundaries can be extracted more accurately without greatly increasing the amount of calculation.

Figure 8:
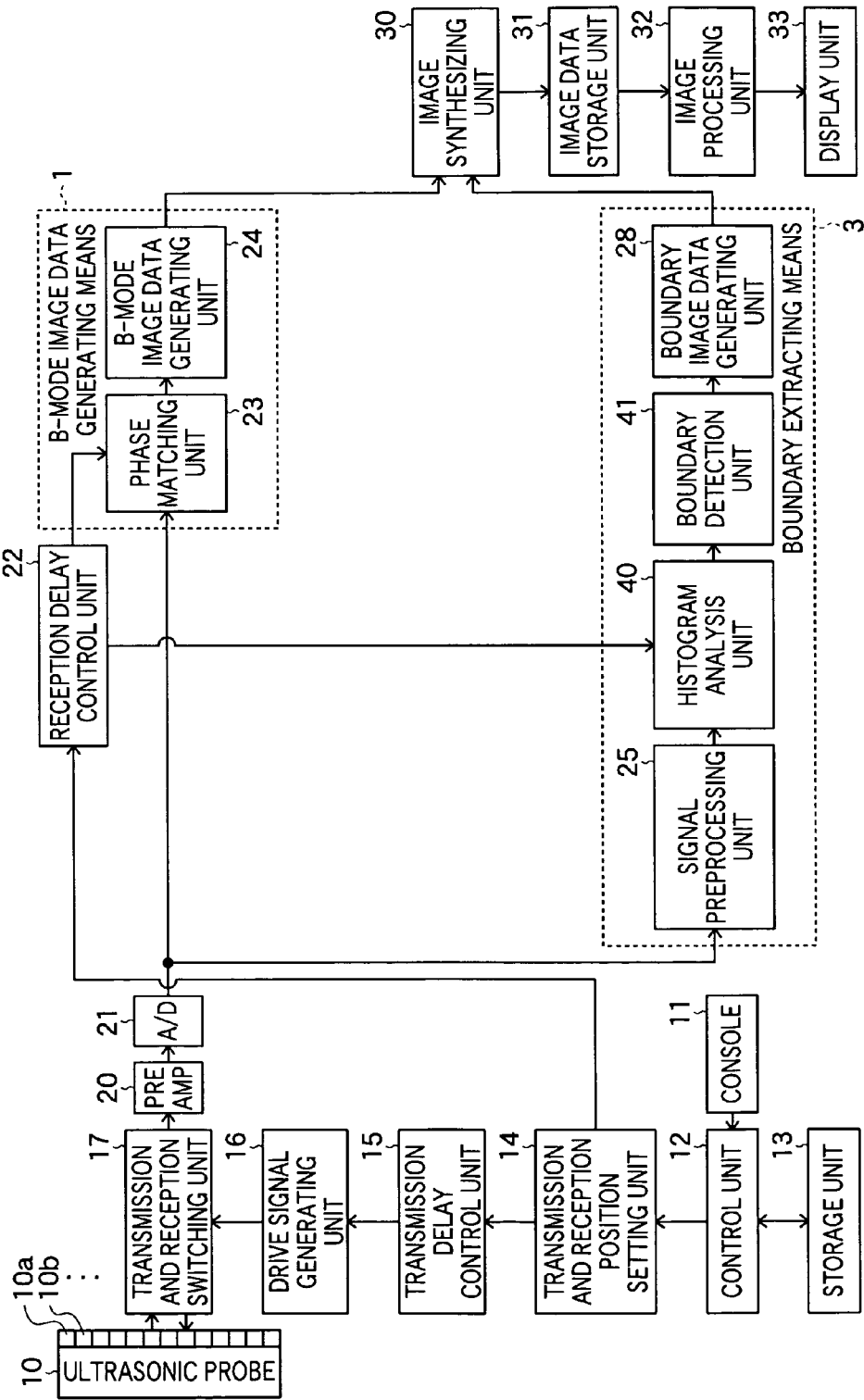
FIG. 8 is a block diagram showing a constitution of an ultrasonic imaging apparatus according to the second embodiment of the present invention.

Next, an ultrasonic imaging apparatus according to the second embodiment of the present invention will be described. FIG. 8 is a block diagram showing a constitution of the ultrasonic imaging apparatus according to the embodiment.

As shown in FIG. 8, this ultrasonic imaging apparatus has boundary extracting means 3 in place of the boundary extracting means 2 in the ultrasonic imaging apparatus shown in FIG. 1. Other constitution is the same as that of the ultrasonic imaging apparatus shown in FIG. 1.

The boundary extracting means 3 includes a signal preprocessing unit 25, a histogram analysis unit 40, and a boundary detection unit 41, and a boundary image data generating unit 28.

The histogram analysis unit 40 generates a histogram based on plural reception signals on the same phase matching line of the plural reception signals that have been intensity corrected by the signal preprocessing unit 25, and thereby, calculates statistics values representing tissue property characteristics of a reflector. Further, the boundary detection unit 41 generates boundary image data using the calculated statistics values as parameters. By the way, the operation of the signal preprocessing unit 25 and the boundary image data generating unit 28 is the same as has been described in the first embodiment.

As below, an operation of the histogram analysis unit 40 and the boundary detection unit 41 will be described in detail.

Figure 9:
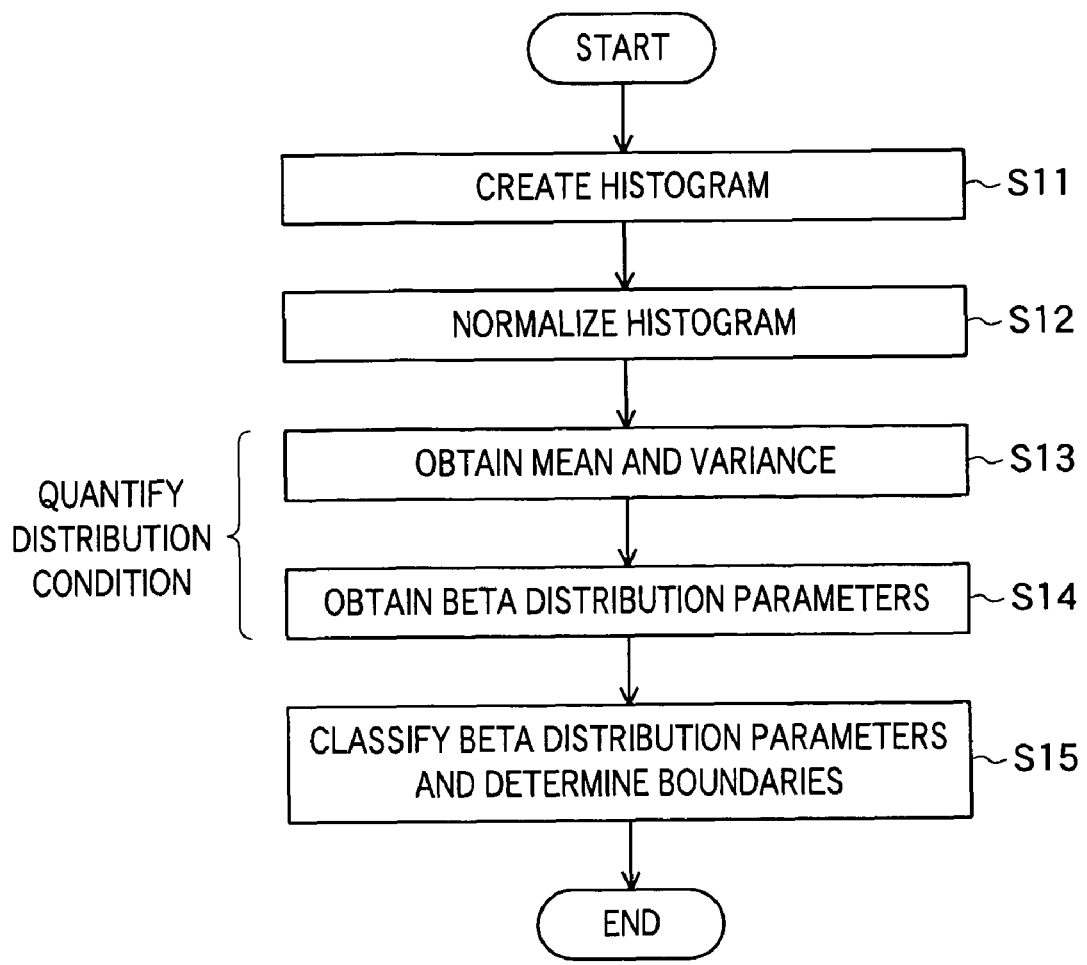
FIG. 9 is a flowchart showing an operation of a histogram analysis unit and a boundary image data generating unit according to a first example.

FIG. 9 is a flowchart showing an operation of the histogram analysis unit 40 and the boundary detection unit 41 according to a first example.

Figure 10A:
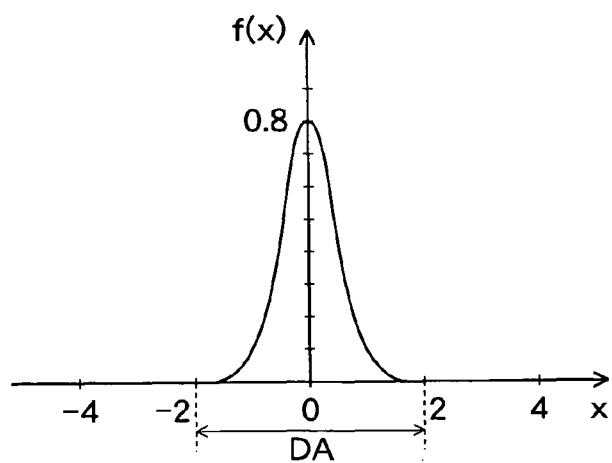
FIGS. 10A and 10B show a spatial intensity distribution of reception signals and a histogram created based thereon.
Figure 10B:
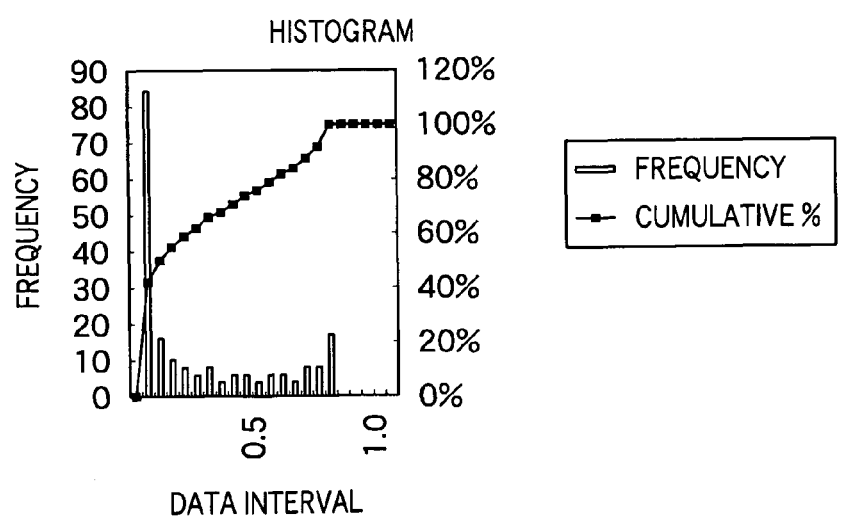

At step S1 in FIG. 9, the histogram analysis unit 40 obtains an intensity distribution as shown in FIG. 10A with respect to reception signals on a region as a target of analysis (analysis region) on a reflector, and further, creates a histogram shown in FIG. 10B based on the intensity distribution. Here, FIG. 10A shows the intensity distribution of reception signals output from plural ultrasonic transducers within aperture diameter DA of an ultrasonic transducer array.

Then, at step S12, the histogram analysis unit 40 normalizes the created histogram so that the range of values (the horizontal axis of the histogram) may be "0" to "1".

Then, at steps S13 and S14, the histogram analysis unit 40 quantifies the distribution condition of the normalized histogram using a beta distribution. The beta distribution is expressed using shape parameters α and β by X~B(α,β), and probability density function f(x) in the beta distribution, r-th moment (product moment) about origin, mean E(x), variance VAR(x), and mode MOD are expressed by the following expressions (1) to (5).

$$f(x) = \frac{1}{B(\alpha, \beta)} x^{\alpha-1}(1-x)^{\beta-1} \quad (0 \le x \le 1) \tag{1}$$

$$\mu_r = \frac{B(\alpha+r, \beta)}{B(\alpha, \beta)} \quad (r \ge 1) \tag{2}$$

$$E(x) = \frac{\alpha}{\alpha+\beta} \tag{3}$$

$$VAR(x) = \frac{\alpha\beta}{(\alpha+\beta)^2(\alpha+\beta+1)} \tag{4}$$

$$MOD = \frac{\alpha-1}{\alpha+\beta-2} \quad (\alpha > 1, \beta > 1) \tag{5}$$

In order to obtain the beta distribution, first, at step S13, sample mean $x_{AVE}$ and variance $\sigma^2$ are obtained using the following expressions (6) and (7) from the normalized histogram.

$$x_{AVE} = \frac{1}{N}\sum_{i=1}^{n} f_i m_i \tag{6}$$

$$\sigma^2 = \frac{1}{N}\sum_{i=1}^{n} f_i m_i^2 - X_{AVE}^2 \tag{7}$$

Then, at step S14, beta distribution parameters α and β are obtained by estimation according to a moment method using the following expressions (8) and (9).

$$\alpha : x_{AVE}\left\{\left[x_{AVE}(1-x_{AVE})\Big/\left(\frac{n-1}{n}\right)\sigma^2\right]-1\right\} \tag{8}$$

$$\beta : (1-x_{AVE})\left\{\left[x_{AVE}(1-x_{AVE})\Big/\left(\frac{n-1}{n}\right)\sigma^2\right]-1\right\} \tag{9}$$

Thereby, an approximate distribution to the beta distribution is obtained.

At step S15, as shown in FIG. 11, the boundary detection unit 41 classifies the beta distribution parameters and determines the respective analysis regions are boundaries or not according to the values of α and β. In this regard, boundary property may be obtained. Here, "U-shaped", "J-shaped", and "single-peaked" in FIG. 11 represent shapes of the probability density function in the beta distribution.

(i) The Case Where α<1 and β<1

Figure 12A:
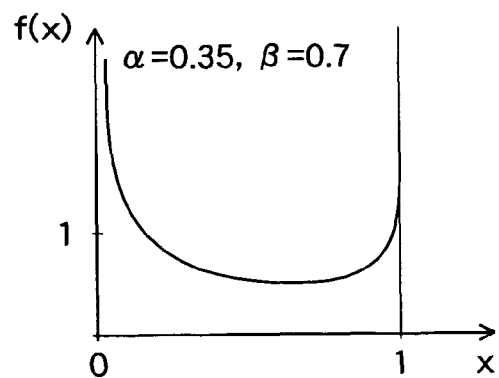
FIGS. 12A to 12C show the cases where beta distributions become U-shaped.
Figure 12B:
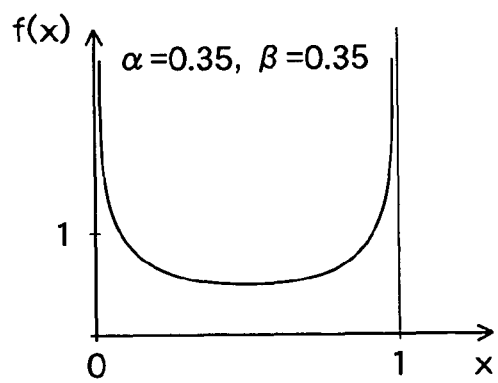
Figure 12C:
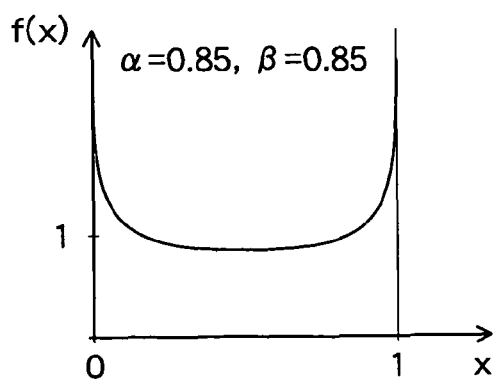

In this case, as shown in FIGS. 12A to 12C, the probability density function f(x) becomes U-shaped. This represents that the peak rises in the intensity distribution of reception signals as shown in FIG. 10A and the reflection surface specularly reflects ultrasonic waves. Further, as shown in FIG. 12A or 12B, since the smaller the value |α×β|, the steeper the U-shaped gradient of the probability density function f(x) becomes, the specular reflectance of reflection surface becomes stronger. Contrary, as shown in FIG. 12C, since the larger the value |α×β|, the gentler the U-shaped gradient of the probability density function becomes, the specular reflection of reflection surface becomes weaker. Accordingly, the boundary detection unit 41 detects the analysis region where the probability density function f(x) becomes U-shaped as a boundary and adds strength of specular reflection to the boundary information according to the value of |α×|.

(ii) The Case Where $(\alpha-1) \times (\beta-1) \leq 0$

Figure 13A:
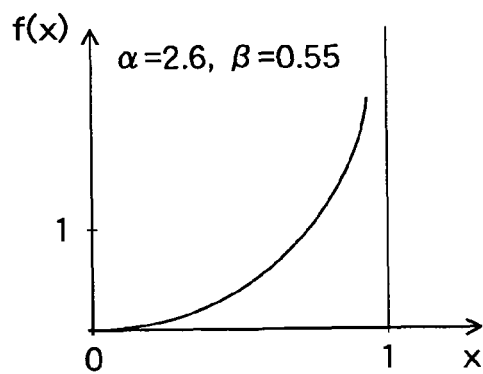
FIGS. 13A to 13D show the cases where beta distributions become J-shaped.
Figure 13B:
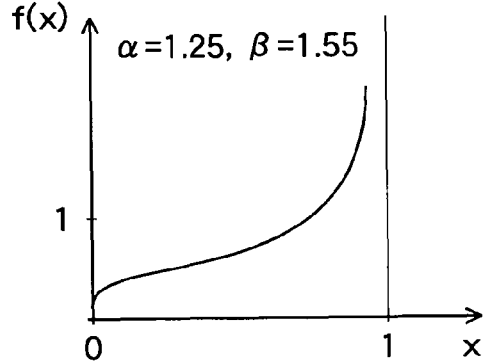
Figure 13C:
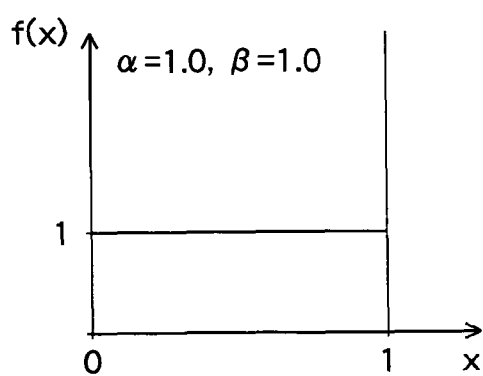
Figure 13D:
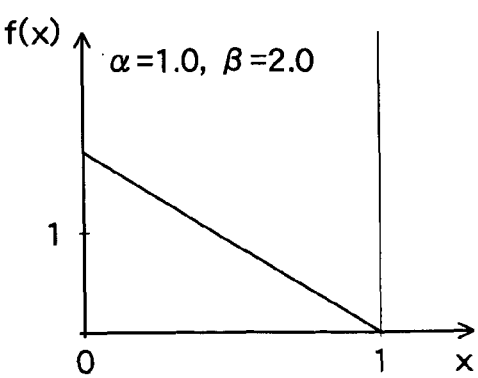

In this case, as shown in FIGS. 13A to 13D, the probability density function becomes J-shaped. This represents that the specular reflection has a peak rising to some degree in the intensity distribution of reception signals and the peak center of intensity resides outside of the aperture of the transducer array. That is, it shows that the reflection surface of specular reflector is inclined relative to the ultrasonic transducer array. For example, in the case where the intensity distribution shown in FIG. 14 is obtained, the histogram changes as shown in FIGS. 15A to 15D by varying the aperture diameter DA of the ultrasonic transducers. Further, as shown in FIG. 13A or 13B, since the more distant from "1" the value |α/β|, the steeper the gradient of the J-shape becomes, the specular reflection of reflection surface becomes stronger. Contrary, as shown in FIG. 13C or 13D, since the closer to "1" the value |α/β|, the gentler the gradient of the J-shape becomes (e.g., gradient "0"), the specular reflection of reflection surface becomes weaker. Accordingly, the boundary detection unit 41 detects the analysis region where the probability density function f(x) becomes J-shaped as a boundary and adds strength of specular reflection to the boundary information according to the value of |α/β|.

(iii) The Case Where $\alpha>1$ and $\beta>1$

Figure 16A:
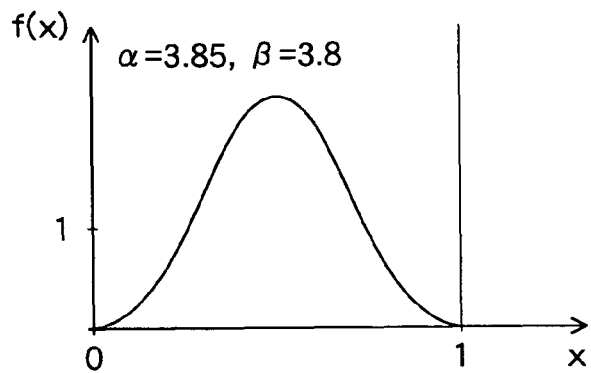
FIGS. 16A to 16C show the cases where beta distributions become single-peaked.
Figure 16B:
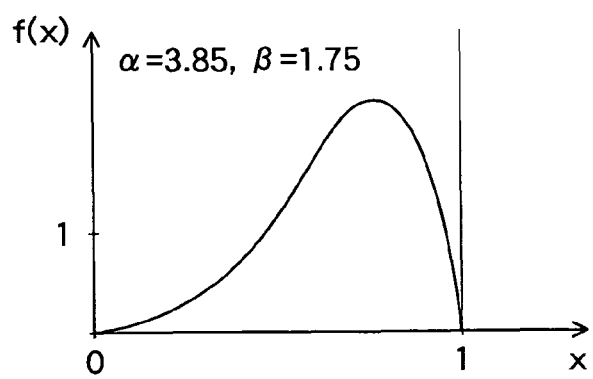
Figure 16C:
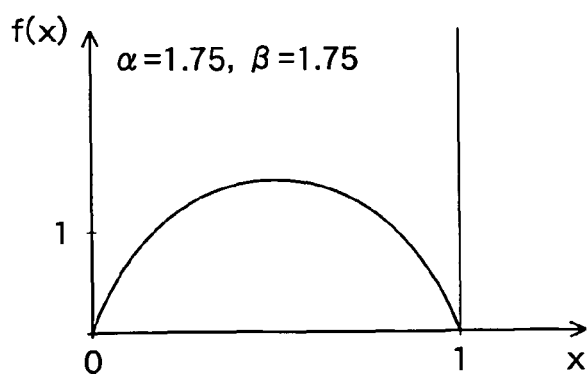

In this case, as shown in FIGS. 16A to 16C, the probability density function f(x) becomes single-peaked. That is, this represents that the intensity distribution of reception signals is a normal distribution and the reflector is a tissue that scatter reflects ultrasonic waves. Further, as shown in FIG. 16A or 16B, the larger the value |α×β|, the steeper the peak of the probability density function f(x) becomes, and that represents a uniform diffusion surface with small variation in intensity distribution. Contrary, as shown in FIG. 16C, the smaller the value |α×β| becomes, the gentler the peak of the probability density function f(x) becomes, and the variation in intensity distribution becomes larger. Or, a region where the value |α×β| is smaller than a certain set threshold value, that often represents speckle components Such an analysis region is not determined as a boundary.

Next, an operation of the histogram analysis unit 40 and the boundary detection unit 41 (FIG. 8) according to a second example will be described.

In this example, in the same manner as have been described in the first example, the histogram analysis unit 40 obtains an intensity distribution with respect to reception signals on the analysis region and creates a histogram, and calculates various statistics values based on a histogram obtained by normalizing that histogram. As the statistics values, mode, median, quartile deviation, skewness, frequency, etc. are used. Here, the quartile deviation is an indicator representing the degree of scattering of frequency, and the quartile deviation QR is obtained by the following expression using the first quartile $X_{0.25}$ and the third quartile $X_{0.75}$. The quartile is a value in a position where the frequency is divided into quarters when data is aligned in ascending order, and the first quartile is a value located at 25% in ascending order and the third quartile is a value located at 75% in ascending order.

$$QR = (X_{0.75} - X_{0.25})/2$$

Further, other statistics values are the same as those have been described in the first embodiment.

Then, the boundary detection unit 41 determines whether or not each analysis region is a boundary based on the calculated statistics values. Further, boundary property of may be simultaneously obtained.

(i) The Case where Variance $\sigma^2$, Quartile Deviation, or Skewness is Smaller than a Threshold Value In a condition in which frequency distribution is concentrated on the vicinity of the mean, these statistics values become smaller. In this case, the analysis region is regarded as scatter reflection surface. In this case, the beta distribution becomes a normal distribution (single-peaked).

(ii) The Case where Variance $\sigma^2$, Quartile Deviation, or Skewness is Larger than a Threshold Value In a condition in which the variation from the mean of the frequency distribution is large, these statistics values become larger. In this case, the boundary detection unit 41 detects the analysis region as a boundary and generates boundary information such that the specular reflectance becomes stronger as the statistics value is larger. In this case, the beta distribution becomes U-shaped or J-shaped.

Here, in the above (i) and (ii), for example, as the curve (3) in FIG. 5, the respective statistics values when the frequency has a uniform distribution are used as threshold values.

Figure 17:
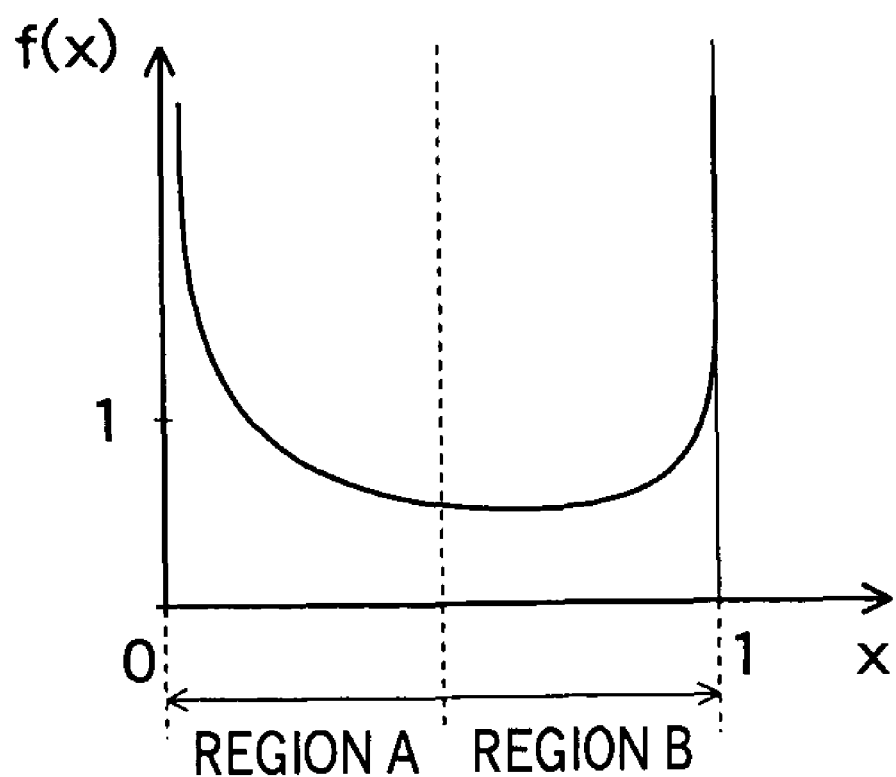
FIG. 17 is a diagram for explanation of an operation of a histogram analysis unit and a boundary image data generating unit according to a third example.

Next, an operation of the histogram analysis unit 40 and the boundary detection unit 41 (FIG. 8) according to a third example will be described. In this example, the histogram analysis unit 40 obtains a beta distribution in the same manner as have been described in the first example. Further, the boundary detection unit 41 selects statistics values to be used according to the shape of the beta distribution and determines whether a region is a boundary or not. That is, in the case where the shape of the beta distribution is single-peaked, because the analysis region can be considered as a scatter reflection surface, variance is used as a parameter. On the other hand, as shown in FIG. 17, in the case where the shape of the beta distribution is U-shaped, the data is divided into two at the broken line in the drawing, and an average value of variances calculated with respect to the regions A and B is used as a parameter.

When the shape is recognized, pattern matching, similarity determination using the least-square method, or similarity determination to theoretical figures of statistics parameters may be performed. In this case, mode, median, rth moment about mean can be used as the statistics parameters.

Figure 18:
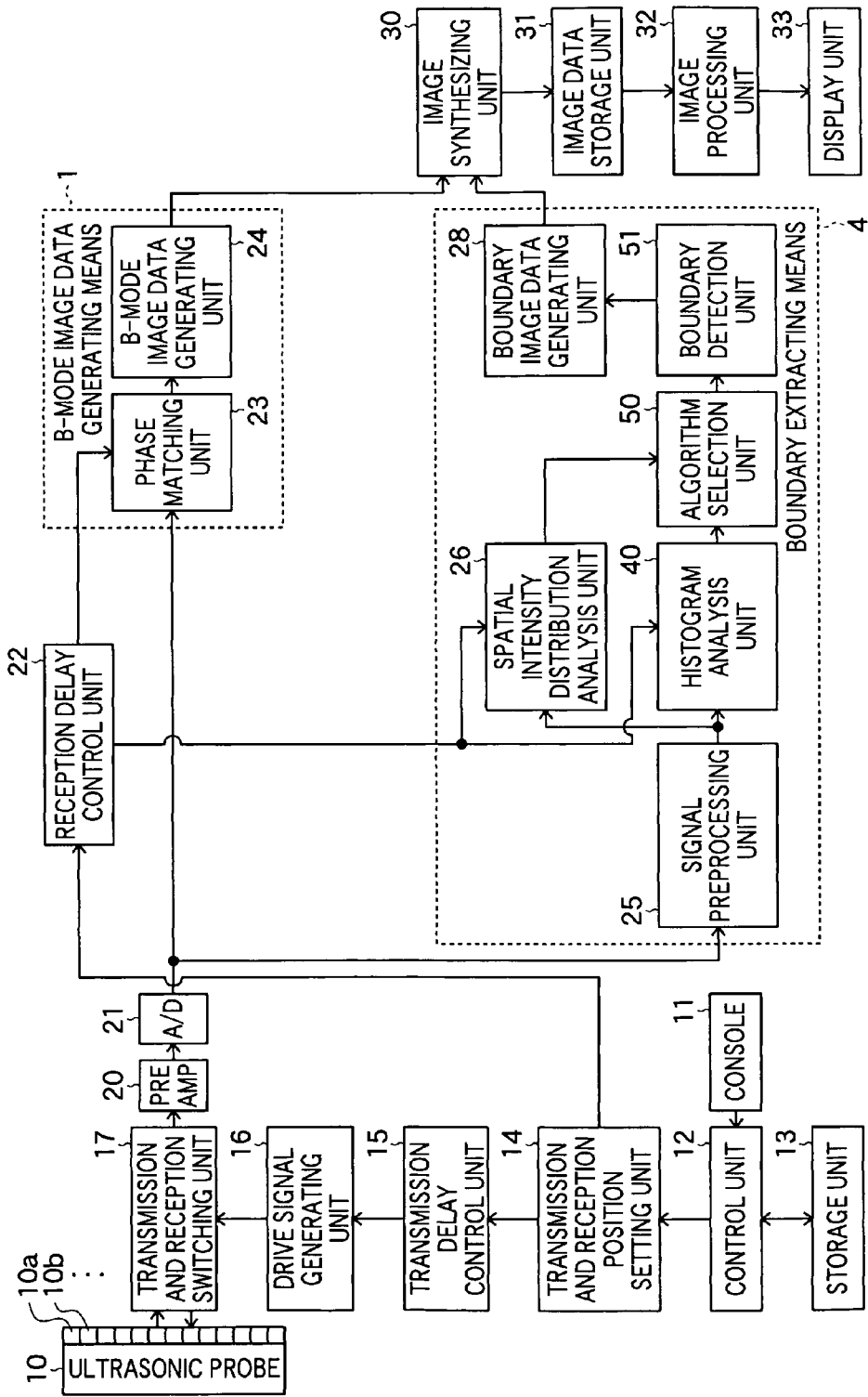
FIG. 18 is a block diagram showing a constitution of an ultrasonic imaging apparatus according to the third embodiment of the present invention.

Next, an ultrasonic imaging apparatus according to the third embodiment of the present invention will be described. FIG. 18 is a block diagram showing a constitution of the ultrasonic imaging apparatus according to the embodiment.

As shown in FIG. 18, the ultrasonic imaging apparatus has boundary extracting means 4 in place of the boundary extracting means 2 shown in FIG. 1. Other constitution is the same as that of the ultrasonic imaging apparatus shown in FIG. 1.

The boundary extracting means 4 further has a histogram analysis unit 40 and an algorithm selection unit 50 compared to the boundary extracting means 2 shown in FIG. 1, and a boundary detection unit 51 in place of the boundary detection unit 27.

The algorithm selection unit 50 provides a statistics value to be used for generating surface property image data and an algorithm for surface property image data generation corresponding to the kind of the statistics value from the statistics value (spatial intensity distribution analysis information) obtained by the analysis in the spatial intensity distribution analysis unit 26 and the statistics value (histogram analysis information) obtained by the analysis in the histogram analysis unit 40 to the boundary detection unit 51. The boundary detection unit 51 generates boundary information by processing the statistics value using the provided algorithm and detecting a boundary. The algorithms corresponding to the kinds of the statistics values are the same as those have been described in the first and second embodiments of the present invention. Further, the operation of the histogram analysis unit 40 is the same as have been described in the second embodiment of the present invention.

Which of the spatial intensity distribution analysis information and the histogram analysis information is used may be set in advance according to conditions such as the number of reception signals depending on the aperture of the ultrasonic transducer array, the intensity of transmitted ultrasonic beam, etc. Further, the use of a combination of the spatial intensity distribution analysis information and the histogram analysis information may be set in advance according to the kind of statistics value. For example, the spatial intensity distribution analysis information is used when whether a region is a boundary or not is determined, and the histogram analysis information is used when boundary property are obtained. Alternatively, the statistics value to be used may be selected by the command of the operator input using the console 11. In this case, the operator may input commands while watching an ultrasonic image displayed on the display unit 33.

Thus, the use of combinations of the spatial intensity distribution analysis information and the histogram analysis information enables efficient extraction of correct boundaries and display of ultrasonic images more suitable for diagnoses.

Figure 19:
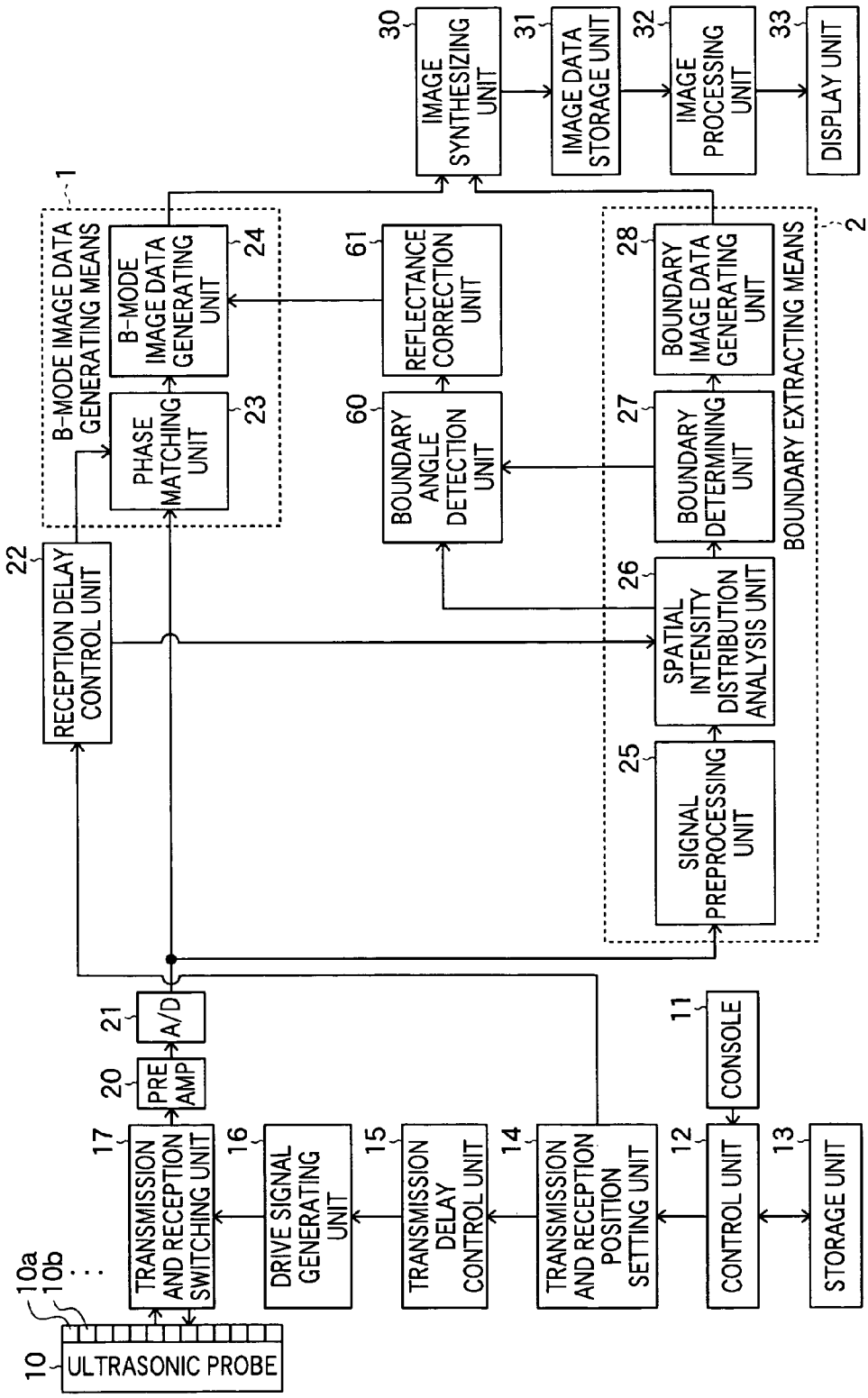
FIG. 19 is a block diagram showing a constitution of an ultrasonic imaging apparatus according to the fourth embodiment of the present invention.

Next, an ultrasonic imaging apparatus according to the fourth embodiment of the present invention will be described. FIG. 19 is a block diagram showing a constitution of the ultrasonic imaging apparatus according to the embodiment.

As shown in FIG. 19, this ultrasonic imaging apparatus further has a boundary angle detection unit 60 and a reflectance correction unit 61 compared to the ultrasonic imaging apparatus shown in FIG. 1. Other constitution is the same as that of the ultrasonic imaging apparatus shown in FIG. 1.

Here, referring FIGS. 2A and 4A again, the case where ultrasonic beams with the same intensity are transmitted to specular reflectors 101 and 103 having the same surface property will be considered. Compared to the case shown in FIG. 2A, as shown in FIG. 4A, when the specular reflector 103 is inclined relative to the incident direction of the ultrasonic beam, because the ultrasonic beam is reflected in a direction different from the incident direction, the case where only part of the beam is received by the ultrasonic transducers 10a, 10b, . . . occurs. As a result, the intensity of reception signals becomes small, and thereby, despite the essentially strong specular reflector, it is only recognized as a weak diffusion distribution. Accordingly, in the embodiment, data values are corrected based on the inclination of the reflector so that B-mode image data may represent real reflectance of reflector surfaces.

The boundary angle detection unit 60 detects an angle relative to the ultrasonic wave transmission direction (i.e., inclination of the boundary surface relative to the ultrasonic transducer array) with respect to the boundary detected by the boundary detection unit 27. In this regard, a statistics value such as a mode or kurtosis calculated with respect to the boundary as a detection target is uses as a parameter. For example, the case where the mode is zero represents that the boundary is not inclined as shown in FIG. 2A, and the larger the absolute value of the mode, the larger the angle of the boundary as shown in FIG. 4A.

Further, the reflectance correction unit 61 obtains an amount of correction for correcting a B-mode image data based on the angle detected by the boundary angle detection unit 60, and provides it to the B-mode image data generating unit 24. The reflectance correction unit 61 has a table for reflectance correction in which amounts of correction corresponding to angles of boundaries are stored, and obtains an amount of correction by referring to the table for reflectance correction. For example, when the boundary is not inclined, the amount of reflectance correction becomes zero, and the larger the angle of the boundary, the larger the amount of reflectance correction becomes. The B-mode image data generating unit 24 performs correction to increase the signal intensity (i.e., brightness on the display screen) on the B-mode image data according to the provided amount of correction.

Such a table for reflectance correction can be created by performing measurement and simulation using a standard reflection source, for example.

Thus, according to the embodiment, the real reflectance, i.e., the accurate difference in acoustic impedance can be displayed as a B-mode image.

Next, a modified example of the ultrasonic imaging apparatus according to the embodiment will be described.

The boundary angle detection unit 60 and the reflectance correction unit 61 shown in FIG. 19 may be provided to the ultrasonic imaging apparatus according to the second embodiment of the present invention shown in FIG. 8. In this case, the boundary angle detection unit 60 may detect an angle of a boundary angle based on the statistics value (such as a mode or kurtosis) calculated from a histogram created by the histogram analysis unit 40, or detect a boundary angle based on the shape of a beta distribution.

Furthermore, the boundary angle detection unit 60 and the reflectance correction unit 61 shown in FIG. 19 may be provided to the ultrasonic imaging apparatus according to the third embodiment of the present invention shown in FIG. 18.

Figure 20:
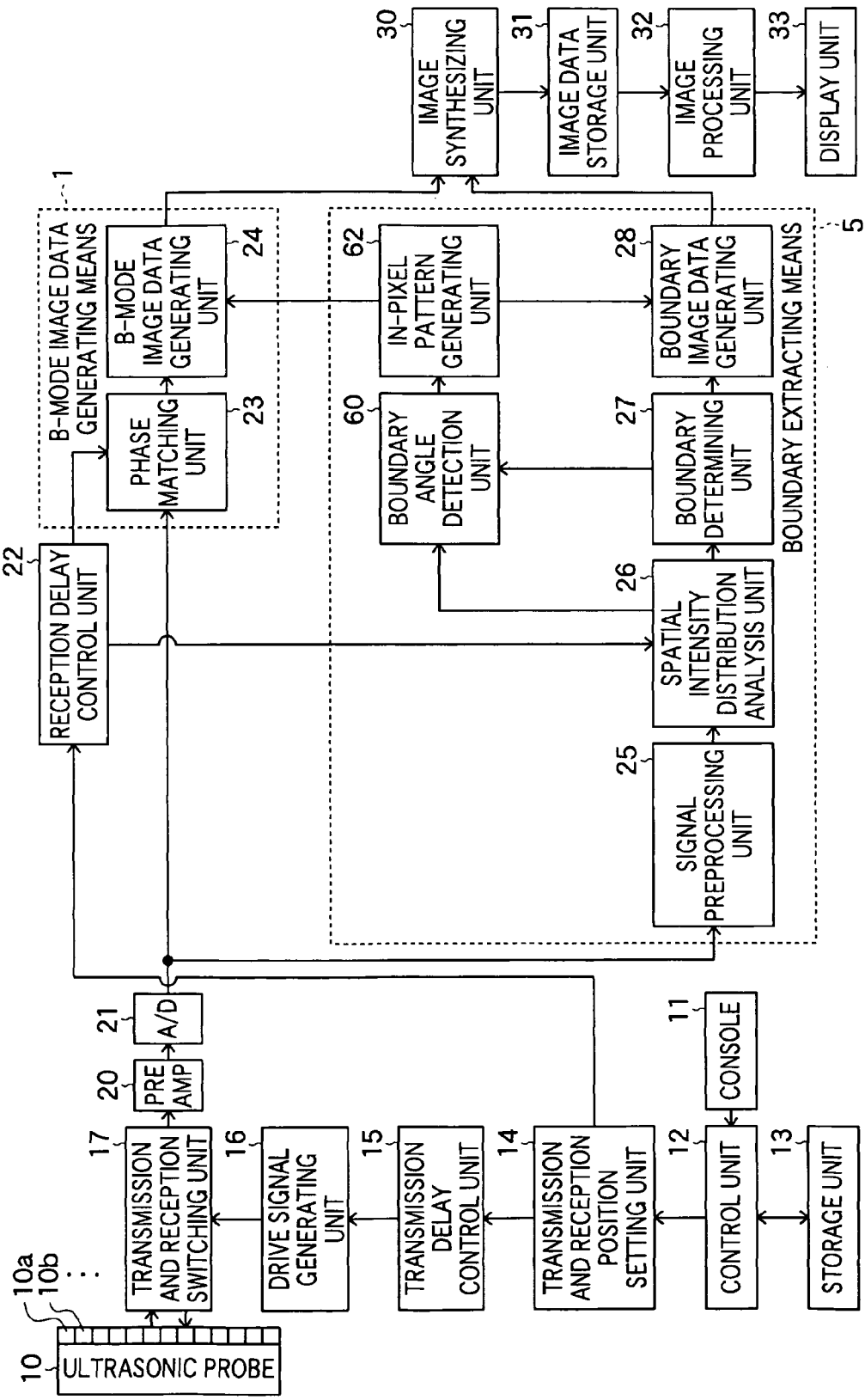
FIG. 20 is a block diagram showing a constitution of an ultrasonic imaging apparatus according to the fifth embodiment of the present invention.

Next, an ultrasonic imaging apparatus according to the fifth embodiment of the present invention will be described. FIG. 20 is a block diagram showing a constitution of the ultrasonic imaging apparatus according to the embodiment.

As shown in FIG. 20, this ultrasonic imaging apparatus has boundary extracting means 5 in place of the boundary extracting means 2 shown in FIG. 1. Other constitution is the same as that of the ultrasonic imaging apparatus shown in FIG. 1.

The boundary extracting means 5 further has a boundary angle detection unit 60 and an intra-pixel pattern generating unit 62 compared to the boundary extracting means 2 shown in FIG. 1.

Figure 21:
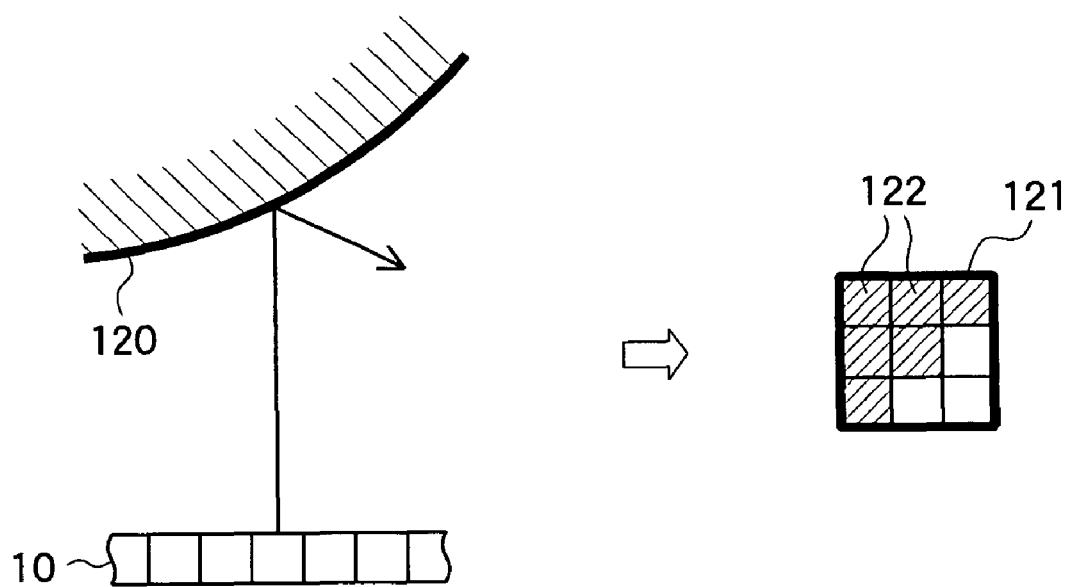
FIG. 21 is a diagram for explanation of an operation of an intra-pixel pattern generating unit shown in FIG. 20.

The intra-pixel pattern generating unit 62 generates an intra-pixel pattern according to a boundary angle of detected by the boundary angle detection unit 60, and supplies it to the B-mode image data generating unit 24 and the boundary image data generating unit 28. For example, as shown in FIG. 21, when a boundary 120 is inclined relative to the ultrasonic transducer array 10, the intra-pixel pattern generating unit 62 divides one pixel 121 into plural micro dot patterns 122 and sets predetermined micro dot patterns (shaded area) to be provided with predetermined brightness signals and color signals. The B-mode image data generating unit 24 and the boundary image data generating unit 28 generate B-mode image data and boundary image data with respect to the position of the boundary according to the provided intra-pixel pattern, respectively. The operation of the boundary angle detection unit 60 is the same as have been described in the fourth embodiment of the present invention.

Thus, formation of a pattern within pixels corresponding to the position of a boundary can improve apparent resolving power in the ultrasonic image.

In the embodiment, the boundary angle detection unit 60 and the intra-pixel pattern generating unit 62 are provided to the ultrasonic imaging apparatus according to the first embodiment of the present invention (FIG. 1), however, they may be similarly provided to the ultrasonic imaging apparatuses according to the second and third embodiments of the present invention (FIGS. 8 and 18). Further, the intra-pixel pattern generating unit 62 may be added to the ultrasonic imaging apparatus according to the fourth embodiment of the present invention (FIG. 19).

Figure 22:
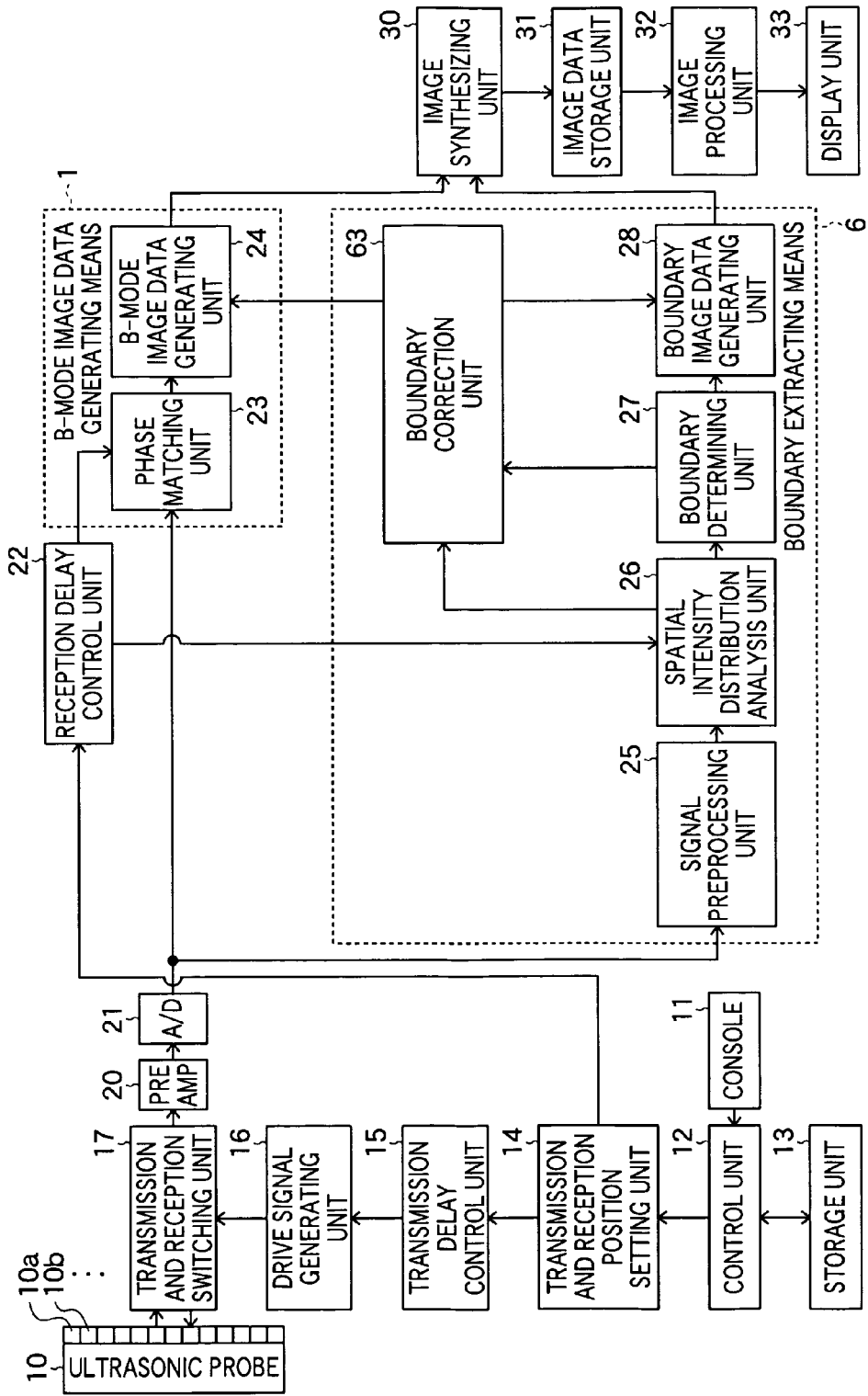
FIG. 22 is a block diagram showing a constitution of an ultrasonic imaging apparatus according to the sixth embodiment of the present invention.

Next, an ultrasonic imaging apparatus according to the sixth embodiment of the present invention will be described. FIG. 22 is a block diagram showing a constitution of the ultrasonic imaging apparatus according to the embodiment.

As shown in FIG. 22, this ultrasonic imaging apparatus has boundary extracting means 6 in place of the boundary extracting means 2 shown in FIG. 1. Other constitution is the same as that of the ultrasonic imaging apparatus shown in FIG. 1. The boundary extracting means 6 further has a boundary correction unit 63 compared to the boundary extracting means 2 shown in FIG. 1.

Figure 23:
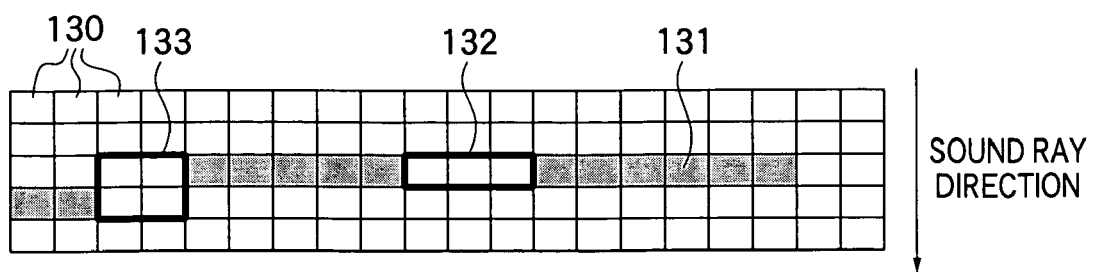
FIG. 23 is a diagram for explanation of an operation of a boundary correction unit shown in FIG. 22.

FIG. 23 is a diagram for explanation of an operation of the boundary correction unit 63. In FIG. 23, pixels 131 (gray regions) show a boundary that has been detected by the boundary detection unit 27 of plural pixels 130 forming an ultrasonic image.

Here, the boundary detection unit 27 detects a boundary by determining whether the respective analysis regions on sound rays are boundaries or not. Accordingly, depending on scanning density or resolving power of ultrasonic beams, like regions 132 and 133, they are not determined as boundaries even though they really are boundaries. As a result, it is likely that an unnatural image between pixels aligned along the horizontal direction (the direction perpendicular to the sound ray direction) might be generated.

Therefore, when accumulating sound ray data for one screen, the boundary correction unit 63 analyzes the continuity of the boundary between adjacent pixels in the horizontal direction or diagonal direction. In the case where a boundary for plural pixels continues and then the boundary is disrupted for several pixels, connecting processing for connecting the boundary is performed while considering the disrupted pixel regions as the boundary. The B-mode image data generating unit 24 and the boundary image data generating unit 28 generate B-mode image data and boundary image data with respect to the regions considered as the boundary, respectively.

Thus, correction of horizontal continuity of the boundary can improve apparent resolving power in the ultrasonic image.

In the embodiment, the boundary correction unit 63 is provided to the ultrasonic imaging apparatus according to the first embodiment of the present invention (FIG. 1), however, it may be similarly provided to the ultrasonic imaging apparatuses according to the second to fifth embodiments of the present invention. For example, in the case where the boundary correction unit 63 is applied to the fifth embodiment, the apparent resolving power can be further improved by applying an intra-pixel pattern generated according to the angle of the boundary with respect to the boundary-corrected regions in the diagonal direction, and an easily-viewable ultrasonic image can be displayed.

Figure 24:
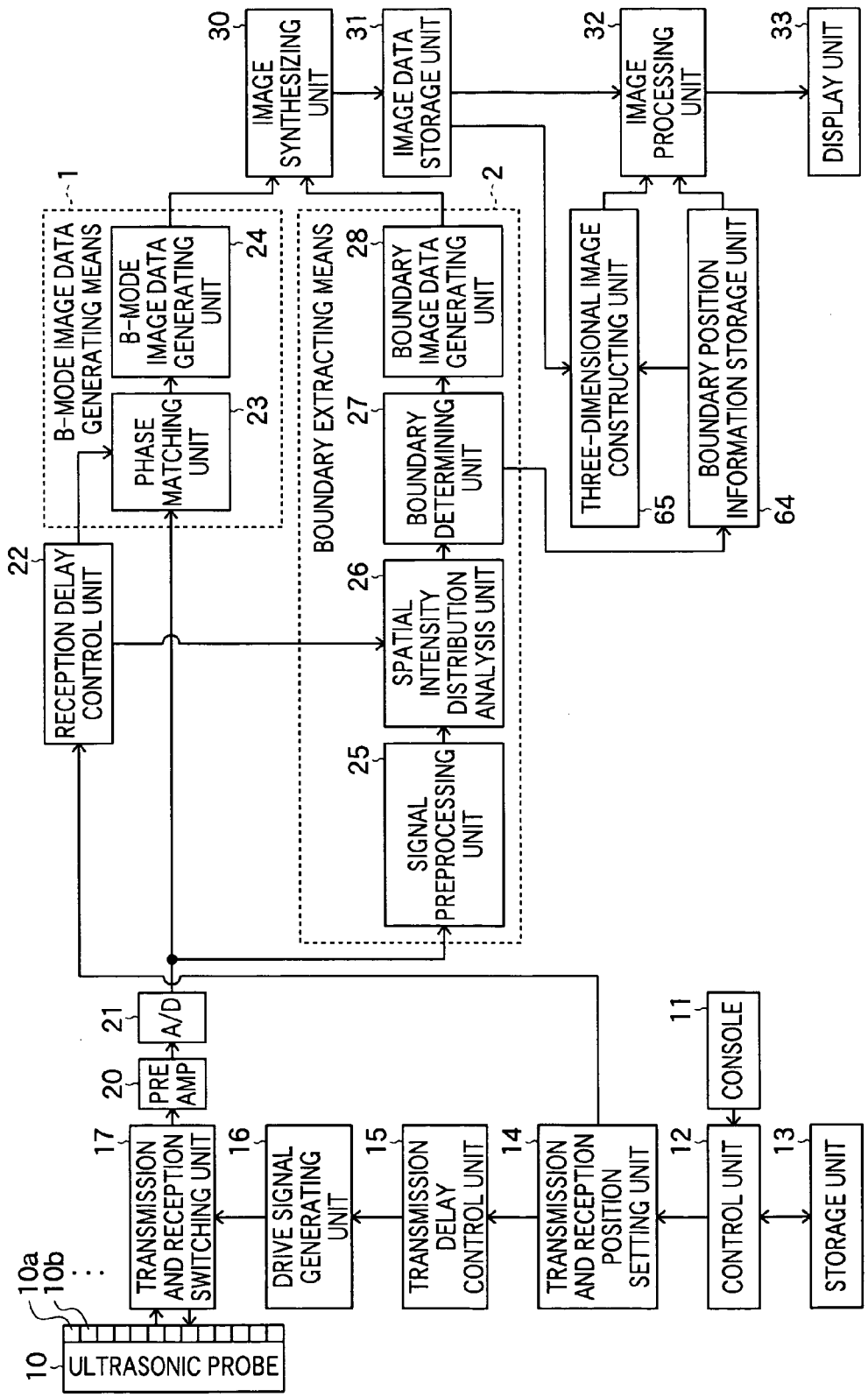
FIG. 24 is a block diagram showing a constitution of an ultrasonic imaging apparatus according to the seventh embodiment of the present invention.

Next, an ultrasonic imaging apparatus according to the seventh embodiment of the present invention will be described. FIG. 24 is a block diagram showing a constitution of the ultrasonic imaging apparatus according to the embodiment.

As shown in FIG. 24, this ultrasonic imaging apparatus is further provided with a boundary position information storage unit 64 and a three-dimensional image constructing unit 65 compared to the ultrasonic imaging apparatus shown in FIG. 1. Other constitution is the same as that of the ultrasonic imaging apparatus shown in FIG. 1.

The boundary position information storage unit 64 stores boundary position information representing positions of boundaries detected by the boundary detection unit 27, and outputs the boundary position information to the three-dimensional image constructing unit 65 according to need. Further, the three-dimensional image constructing unit 65 constructs a three-dimensional image based on plural image data (tomographic image data) stored in the image data storage unit 31. In this regard, the three-dimensional image constructing unit 65 can generate a smooth three-dimensional image by connecting boundaries in the respective tomographic planes based on the boundary position information output from the boundary position information storage unit 64.

Further, when the boundary position information is directly output from the boundary position information storage unit 64 to the image processing unit 32, user-desired image processing can be performed in the image processing unit 32. For example, gradation processing, color correction, or the like can be performed only on a desired region surrounded by a certain boundary (e.g., within a certain tissue).

Furthermore, as a modified example of the ultrasonic imaging apparatus according to the embodiment, the boundary position information stored in the boundary position information storage unit 64 may be output to a computation processing unit added as an advanced feature to the ultrasonic imaging apparatus or an external computation processing unit. In such a computation processing unit or the like, the length, area, volume of a desired region can be calculated using the boundary position information. Those calculated amounts can be utilized when the size or aspect ratio of an organ or a tumor that has been formed therein and surface irregularities as an indicator at the time of determination whether a tumor is benign or malignant are measured. Further, the boundary position information can be used for region determination when statistics values of ultrasonic echo signals are calculated. For example, it is known that, at the time of liver diagnosis, the probability density function of signal amplification follows a Rayleigh distribution in a normal liver, and departs from the Rayleigh distribution in a cirrhotic part.

In the embodiment, the boundary position information storage unit 64 is provided to the ultrasonic imaging apparatus according to the first embodiment of the present invention, however, it may be similarly provided to the ultrasonic imaging apparatuses according to the second to sixth embodiments of the present invention.

As described above, according to the first to seventh embodiments of the present invention, using the interrelationship and property of signals such as spatial intensity distribution and statistics values of the plural reception signals, boundaries in an ultrasonic image can be extracted and imaged in real time by simple calculation. Further, since the respective units utilizing the boundary extracting means as has been described in the first to seventh embodiments of the present invention and boundary information generated there can be added as an advanced feature to a general ultrasonic imaging apparatus, a system can be configured at a low price.

The invention claimed is:

1. An ultrasonic image boundary extracting method comprising the steps of:
   (a) obtaining an interrelationship among plural reception signals with respect to a region within an object to be inspected from among reception signals obtained by transmitting ultrasonic waves toward the object from plural ultrasonic transducers and receiving ultrasonic waves reflected from the object, said interrelationship including at least one of (1) a spatial intensity distribution of the plural reception signals on a same phase matching line and (2) a statistical property among the plural reception signals on the same phase matching line; and
   (b) detecting a boundary between plural different tissues within the object based on said interrelationship to thereby generate information on a tissue boundary.

2. An ultrasonic image boundary extracting method according to claim 1, wherein step (b) includes determining whether the region is a boundary or not, based on the spatial intensity distribution of said plural reception signals on the same phase matching line, and obtaining a boundary property based on the statistical property among said plural reception signals on the same phase matching line.

3. An ultrasonic image boundary extracting method according to claim 1, wherein step (a) includes obtaining the statistical property among said plural reception signals on the same phase matching line by utilizing a beta distribution.

4. An ultrasonic image boundary extracting method according to claim 1, further comprising the step of:
   obtaining a tissue boundary angle relative to the ultrasonic waves transmitted from said plural ultrasonic transducers based on said interrelationship.

5. An ultrasonic image boundary extracting apparatus comprising:
   analysis means for obtaining an interrelationship among plural reception signals with respect to a region within an object to be inspected from among reception signals obtained by transmitting ultrasonic waves toward the object from plural ultrasonic transducers and receiving ultrasonic waves reflected from the object, said interrelationship including at least one of (1) a spatial intensity distribution of the plural reception signals on a same phase matching line and (2) a statistical property among the plural reception signals on the same phase matching line; and
   boundary detecting means for detecting a boundary between plural different tissues within the object based on said interrelationship to thereby generate information on a tissue boundary.

6. An ultrasonic image boundary extracting apparatus according to claim 5, wherein said boundary detecting means determines whether the region is a boundary or not, based on the spatial intensity distribution of said plural reception signals on the same phase matching line, and obtains a boundary property based on the statistical property among said plural reception signals on the same phase matching line.

7. An ultrasonic image boundary extracting apparatus according to claim 5, wherein said analysis means obtains the statistical property among said plural reception signals on the same phase matching line by utilizing a beta distribution.

8. An ultrasonic image boundary extracting apparatus according to claim 5, further comprising:
   boundary angle detecting means for obtaining a tissue boundary angle relative to the ultrasonic waves transmitted from said plural ultrasonic transducers based on said interrelationship.

* * * * *